(12) United States Patent
Puskas

(10) Patent No.: US 7,072,720 B2
(45) Date of Patent: Jul. 4, 2006

(54) DEVICES AND METHODS FOR VAGUS NERVE STIMULATION

(75) Inventor: John D. Puskas, Atlanta, GA (US)

(73) Assignee: Emory University, Atlanta, GA (US)

( * ) Notice: Subject to any disclaimer, the term of this patent is extended or adjusted under 35 U.S.C. 154(b) by 767 days.

(21) Appl. No.: 10/172,377

(22) Filed: Jun. 14, 2002

(65) Prior Publication Data
US 2003/0074039 A1   Apr. 17, 2003

Related U.S. Application Data

(63) Continuation of application No. 09/980,421, filed as application No. PCT/US00/17222 on Jun. 23, 2000.

(60) Provisional application No. 60/141,202, filed on Jun. 25, 1999.

(51) Int. Cl.
*A61N 1/05* (2006.01)
(52) U.S. Cl. .................................... 607/118
(58) Field of Classification Search ............. 607/118, 607/5, 9, 149
See application file for complete search history.

(56) References Cited

U.S. PATENT DOCUMENTS

| | | | |
|---|---|---|---|
| 4,304,239 A | 12/1981 | Perlin | |
| 4,351,330 A | 9/1982 | Scarberry | |
| 4,574,807 A | 3/1986 | Hewson et al. | |
| 4,640,298 A | 2/1987 | Pless et al. | |
| 4,671,295 A | 6/1987 | Abrams et al. | |
| 4,722,347 A | 2/1988 | Abrams et al. | |
| 4,753,244 A | 6/1988 | Landymore et al. | |
| 4,960,133 A | 10/1990 | Hewson | |
| 5,014,698 A | 5/1991 | Cohen | |
| 5,024,228 A | 6/1991 | Goldstone et al. | |
| 5,044,367 A | 9/1991 | Endres et al. | |
| 5,052,390 A | 10/1991 | Hewson | |
| 5,056,519 A | 10/1991 | Vince | |
| 5,056,532 A | 10/1991 | Hull et al. | |
| 5,117,828 A | 6/1992 | Metzger et al. | |

(Continued)

FOREIGN PATENT DOCUMENTS

DE   2811325   9/1979

(Continued)

OTHER PUBLICATIONS

Bufkin, et al., "Controlled Intermittent Asystole: Pharmacologic Potentiation of Vagal-Induced Asystole," *Ann. Thorac. Surg.*, 1998;66: pp. 1185-1190 (Abstract Only).

(Continued)

*Primary Examiner*—George Manuel
*Assistant Examiner*—Dana D. Greene
(74) *Attorney, Agent, or Firm*—Michael Best & Friedrich LLP

(57) ABSTRACT

The present invention relates to apparatus and methods for electrically inducing and pharmacologically maintaining cardiac asystole. The present invention combines electrostimulation of the vagus nerve to transiently arrest the heart, and the administration of a pharmaceutical composition that suppresses the tendency of the heart to escape from the induced asystolic state. The present invention provides an apparatus to interrogate the response of a heart to an electric pulse applied to the vagus nerve and to select the optimum location of an electrode and pulse to arrest the heart. The present invention further provides embodiments of catheter and tube electrode devices that incorporate expanding electrodes intended to contact the interior walls of blood vessels or anatomic structures in which the electrode devices are implanted. The present invention also provides cutaneous array electrodes that may be used non-invasively to stimulate the vagus nerve.

88 Claims, 10 Drawing Sheets

U.S. PATENT DOCUMENTS

| | | | |
|---|---|---|---|
| 5,125,406 A | 6/1992 | Goldstone et al. | |
| 5,127,407 A | 7/1992 | Tan | |
| 5,129,392 A | 7/1992 | Bardy et al. | |
| 5,156,149 A | 10/1992 | Hudrlik | |
| 5,156,151 A | 10/1992 | Imran | |
| 5,199,428 A | 4/1993 | Obel et al. | |
| 5,203,326 A | 4/1993 | Collins | |
| 5,205,285 A | 4/1993 | Baker, Jr. | |
| 5,243,980 A | 9/1993 | Mehra | |
| 5,263,480 A | 11/1993 | Wernicke | |
| 5,265,603 A | 11/1993 | Hudrlik | |
| 5,282,468 A | 2/1994 | Klepinski | |
| 5,284,146 A | 2/1994 | Czar et al. | |
| 5,292,338 A | 3/1994 | Bardy et al. | |
| 5,304,120 A | 4/1994 | Crandell et al. | |
| 5,304,206 A | 4/1994 | Baker, Jr. et al. | |
| 5,330,507 A | 7/1994 | Schwartz | |
| 5,330,515 A | 7/1994 | Rutecki et al. | |
| 5,334,221 A | 8/1994 | Bardy | |
| 5,354,318 A | 10/1994 | Taepke | |
| 5,356,425 A | 10/1994 | Bardy et al. | |
| 5,365,926 A | 11/1994 | Desai | |
| 5,403,356 A | 4/1995 | Hill et al. | |
| 5,411,529 A | 5/1995 | Hudrlik | |
| 5,417,713 A | 5/1995 | Cohen | |
| 5,456,254 A | 10/1995 | Pietroski et al. | |
| 5,501,703 A | 3/1996 | Holsheimer et al. | |
| 5,507,784 A | 4/1996 | Hill et al. | |
| 5,540,730 A | 7/1996 | Terry, Jr. et al. | |
| 5,540,732 A | 7/1996 | Testerman | |
| 5,549,655 A | 8/1996 | Erickson | |
| 5,571,150 A | 11/1996 | Wernicke et al. | |
| 5,578,061 A | 11/1996 | Stroetmann et al. | |
| 5,611,350 A | 3/1997 | John | |
| 5,620,468 A | 4/1997 | Mongeon et al. | |
| 5,651,378 A | 7/1997 | Matheny et al. | |
| 5,656,420 A | 8/1997 | Chien | |
| 5,668,117 A | 9/1997 | Shapiro | |
| 5,690,681 A | 11/1997 | Geddes et al. | |
| 5,713,924 A | 2/1998 | Min et al. | |
| 5,713,929 A | 2/1998 | Hess et al. | |
| 5,782,874 A | 7/1998 | Loos | |
| 5,792,187 A | 8/1998 | Adams | |
| 5,840,076 A | 11/1998 | Swanson et al. | |
| 5,846,263 A | 12/1998 | Peterson et al. | |
| 5,889,033 A | 3/1999 | Kaminski | |
| 5,893,882 A | 4/1999 | Peterson et al. | |
| 5,913,876 A | 6/1999 | Taylor | |
| 5,916,239 A | 6/1999 | Geddes et al. | |
| 6,006,134 A | 12/1999 | Hill et al. | |
| 6,043,273 A | 3/2000 | Duhaylongsod | |
| 6,060,454 A | 5/2000 | Duhaylongsod | |
| 6,087,394 A | 7/2000 | Duhaylongsod | |
| 6,091,988 A | 7/2000 | Warman et al. | |
| 6,101,412 A | 8/2000 | Duhaylongsod | |
| 6,127,410 A | 10/2000 | Duhaylongsod | |
| 6,141,589 A | 10/2000 | Duhaylongsod | |
| 6,185,459 B1 | 2/2001 | Mehra et al. | |
| 6,266,564 B1 | 7/2001 | Hill et al. | |
| 6,272,380 B1 | 8/2001 | Warman et al. | |
| 6,308,104 B1* | 10/2001 | Taylor et al. | 607/118 |
| 6,414,018 B1 | 7/2002 | Duhaylongsod | |
| 6,442,429 B1 | 8/2002 | Hill et al. | |
| 6,449,507 B1 | 9/2002 | Hill et al. | |
| 6,487,446 B1* | 11/2002 | Hill et al. | 604/20 |
| 6,532,388 B1 | 3/2003 | Hill et al. | |
| 6,542,774 B1 | 4/2003 | Hill et al. | |
| 6,554,781 B1 | 4/2003 | Hill et al. | |
| 6,628,987 B1 | 9/2003 | Hill et al. | |
| 6,656,960 B1* | 12/2003 | Puskas | 514/345 |
| 6,690,973 B1* | 2/2004 | Hill et al. | 607/43 |
| 6,718,208 B1 | 4/2004 | Hill et al. | |
| 6,735,471 B1 | 5/2004 | Hill et al. | |
| 6,738,667 B1 | 5/2004 | Deno et al. | |
| 6,778,854 B1* | 8/2004 | Puskas | 607/2 |
| 2003/0216775 A1 | 11/2003 | Hill et al. | |
| 2003/0216790 A1 | 11/2003 | Hill et al. | |
| 2004/0199209 A1 | 10/2004 | Hill et al. | |

FOREIGN PATENT DOCUMENTS

| | | |
|---|---|---|
| EP | 0589252 | 3/1994 |
| WO | WO 92/11064 | 7/1992 |
| WO | WO 97/40885 | 11/1997 |
| WO | WO 9907354 | 8/1998 |
| WO | WO 99/09971 | 3/1999 |
| WO | WO 99/09973 | 3/1999 |
| WO | WO 01/00273 | 1/2001 |

OTHER PUBLICATIONS

DiPiro, et al., "Pharmacotherapy: A Pathophysiologic Approach;" Reed Elsevier, New York; pp. 153-157, (1989).

Hageman, G.R, et al., "Direct and Reflex Cardiac Bradydysrhthmias From Small Vagal Nerve Stimulations," *Am. Heart J.*, vol. 89, No. 3, pp. 338-348 (1975) (Abstract Only).

Matheny, et al., "Vagus Nerve Stimulation as a Method to Temporarily Slow or Arrest the Heart," *Ann. Thorac. Surg.*, 1997:63: pp. 528-529.

Nobrega, et al., "Resting and Reflex Heart Rate Responses During Cholinergic Stimulation With Pyridostigmine in Humans," *Brazilian J. Med. Biol. Res*, vol. 29, No. 11, pp. 1461-1465 (1996) (Abstract Only).

Okazawa, M., et al., "Effect of Vagal Stimulations and Parenteral Acetylcholine on Canine Trachealis Muscle Shortening," *J. Appl. Physiol.*, vol. 75, No. 6, pp. 2463-2468 (1992) (Abstract Only).

Taylor, P., "Anticholinesterase Agents" in Goodman and Gilman's *The Pharmacological Basis of Therapeutics* (6$^{th}$ Ed.), MacMillan Publishing Co., Inc., New York, pp. 104-108 (1980).

Taylor, P., "Cholinergic Agonists" in Goodman and Gilman's *The Pharmacological Basis of Therapeutics* (6$^{th}$ Ed.), MacMillan Publishing Co., Inc., New York, pp. 93-94 (1980).

Thompson, et al., "Bradycardia Induced by Intravascular Versus Direct Stimulation of the Vagus Nerve," *Ann. Thorac. Surg.*, 1998;65: 637-642 (Abstract Only).

Urthaler, James F., "Experimental Studies on the Pathogenesis of Asystole After Verapamil in the Dog," *Am. J. Cardiol.*, vol. 44, No. 4, pp. 651-656 (1979) (Abstract Only).

Annegers, A.F., et al., "Epilepsy, Vagal Nerve Stimulation by the NCP System, All-Cause Morality, and Sudden, Unexpected, Unexplained Death," *Epilepsia*, vol. 41, No. 5, pp. 549-553 (2000).

Barwell, J., et al., "The NIM-2 Nerve Integrity Monitor in Thyroid and Parathyroid Surgery," *British Journal of Surgery*, vol. 84, No. 854, p. 854 (1997).

Ben-Menachem, E., et al., "Vagus Nerve Stimulation for Treatment of Partial Seizures: 1. A Controlled Study of Effect on Seizures," *Epilepsia*, vol. 35, No. 3, pp. 616-626 (1994).

Bilgutay, A., et al., "Vagal Tuning: A New Concept in the Treatment of Supraventricular Arrhythmias, Angina Pectoris, and Heart Failure," *Journal of Thoracic and Cardiovascular Surgery*, vol. 56, No. 1, pp. 71-82 (1968).

Bluemel, K.M., et al., "Parasympathetic Postganglionic Pathways to the Sinoatrial Node," American Physiological Society, pp. H1504-H1510 (1990).

Braunwald, E., et al., "Carotid Sinus Nerve Stimulation in the Treatment of Angina Pectoris and Supraventricular Tachycardia," *The Western Journal of Medicine*, pp. 41-50 (1970).

Carlson, M. et al., "Selective Stimulation of Parasympathetic Nerve Fibers to the Human Sinoatrial Node," *Circulation*, vol. 85, No. 4, pp. 1311-1317 (1992).

Cooper, T., et al., "Neural Effects on Sinus Rate and Atrioventricular Conduction Producted by Electrical Stimulation from a Transvenous Electrode Catheter in the Canine Right Pulmonary Artery," *Circulation Research*, vol. 46, No. 1, pp. 48-57 (1980).

Duhaylongsod, F., et al., "Controlled Ventricular Asystole With Surgeon-Actuated Pacing for Off-Pump Coronary Artery Bypass Grafting: A Proposed Surgical Method," *IBMICS* (1998) (Abstract).

Espinosa, J., et al., "Revision and Removal of Stimulating Electrodes Following Long-Term Therapy with the Vagus Nerve Stimulator," *Surg. Neurol.*, vol. 51, pp. 659-664 (1999).

George, R., et al., "Vagus Nerve Stimulation for Treatment of Partial Seizures: 3. Long-Term Follow-Up on First 67 Patients Exiting a Controlled Study," *Epilepsia*, vol. 35, No. 3, pp. 637-643 (1994).

Jalife, J. et al., "Desensitization of the Cholinergic Receptor at the Sinoatrial Cell of the Kitten," *American Physiological Society*, pp. H439-H448 (1980).

Khanna, R., et al., "Coronary Artery Surgery With Induced Temporary Asystole and Intermittent Ventricular Pacing: An Experimental Study," *Cardiovascular Surgery*, vol. 4, No. 2, pp. 231-236 (1996).

Lagi, A., et al., "Age-Related Changes of Cardiac Parasympathetic Modulation After Vasovagal Syncope," *The American Journal of Cardiology*, vol. 83, pp. 977-980 (1999).

Loeb, J., et al., "Sensitivity Differences of SA and AV Node to Vagal Stimulation: Attenuation of Vagal Effects at SA Node," *American Physiological Society*, pp. H684-H690 (1981).

Maloney, R., et al, "A New Method for Intraoperative Recurrent Laryngeal Nerve Monitoring," *ENT Journal*, vol. 73, No. 1, pp. 30-33 (1994).

Martin, P., et al., "Fade of Cardiac Responses During Tonic Vagal Stimulation," *American Physiological Society*, pp. H219-H225 (1982).

Matheny, R., "Experiences in Minimally Invasive Surgery-Techniques of Stabilization," presented at the Minneapolis Heart Institute Foundation, Jun. 19-21, 1997.

Poller, U., et al., "Age-Dependent Changes in Cardiac Muscarinic Receptor Function in Healthy Volunteers," *Journal of the American College of Cardiology*, vol. 29, No. 1, pp. 187-193 (1997).

Ramsay, R., et al., "Vagus Nerve Stimulation for Treatment of Partial Seizures: 2. Safety, Side Effects, and Tolerability," *Epilepsia*, vol. 35, No. 3, pp. 627-636 (1994).

Randall, W.C., et al., "Functional Anatomy of the Cardiac Efferent Innervation," Neurocardiology, pp. 3-24 (1988).

Sato, I, et al., "Age-Related Changes of Cardiac Control Function in Man," *Journal of Gerontology*, vol. 36, No. 5, pp. 564-572 (1981).

Severtson, M., et al., "Vagal Monitoring: A Comparison of Techniques in a Canine Model," *American Journal of Otology*, vol. 18, pp. 398-400 (1997).

Upton, A., Editorial, *PACE*, vol. 15, Part II, pp. 1543-1544 (1992).

Wilder, B.J., et al., "Vagus Nerve Stimulation for the Control of Epilepsy," *Epilepsia*, vol. 31, Supp. 2, pp. S1-S60 (1990).

\* cited by examiner

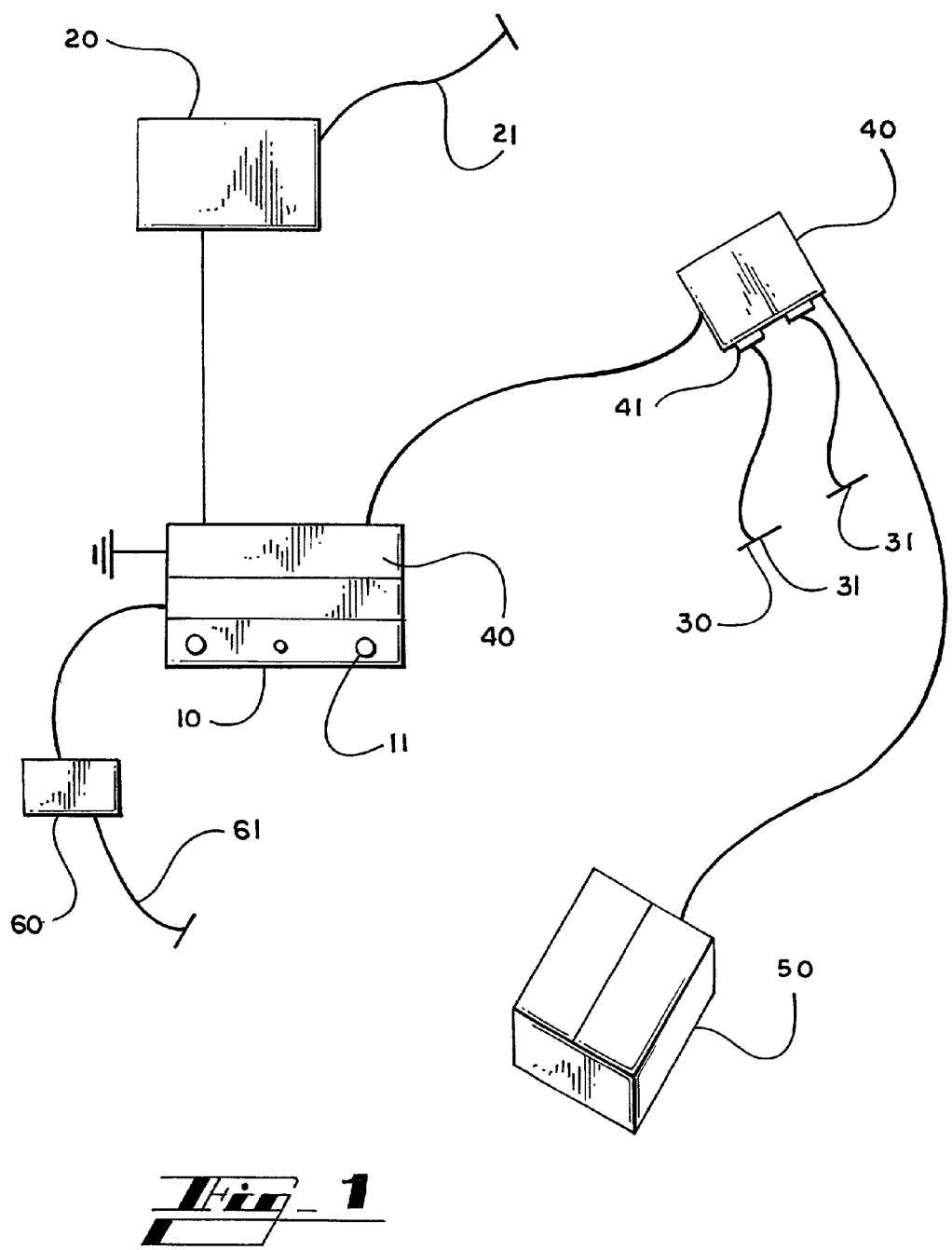
Fig_1

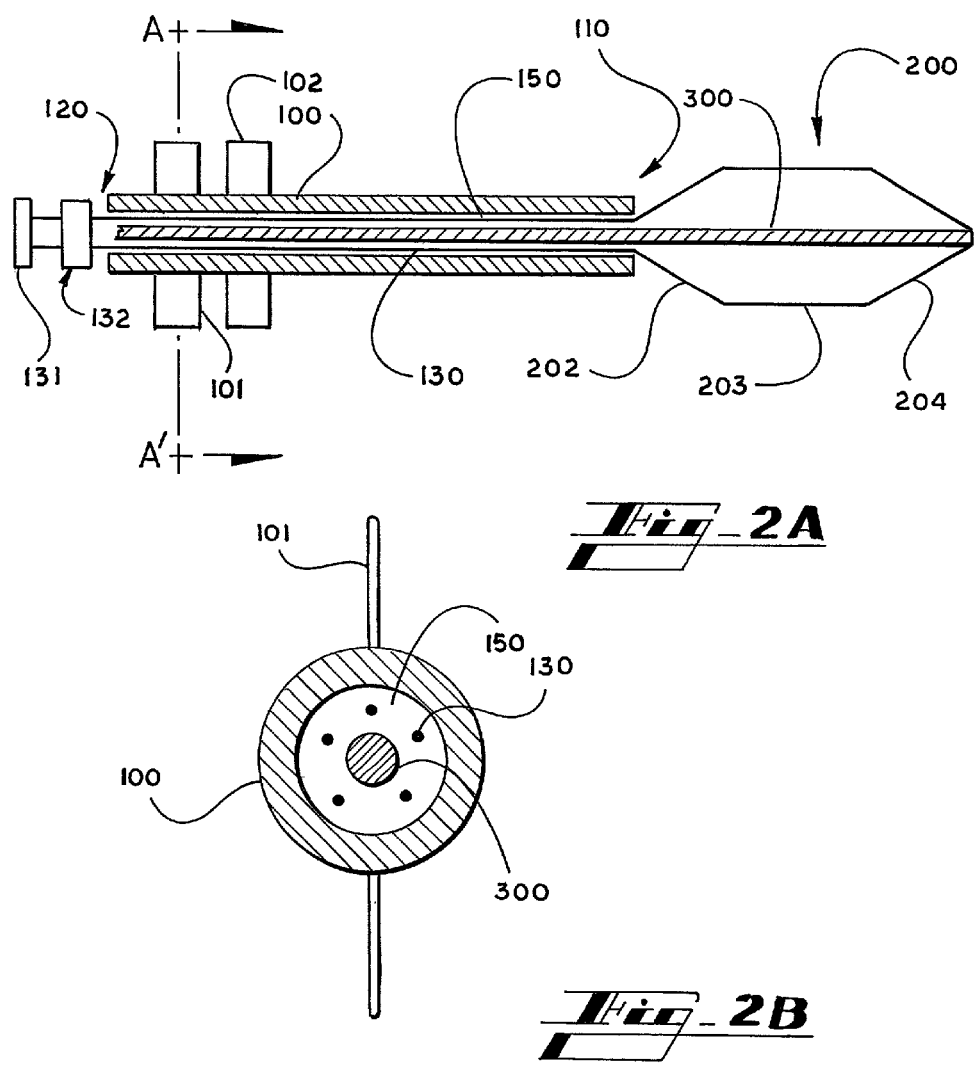

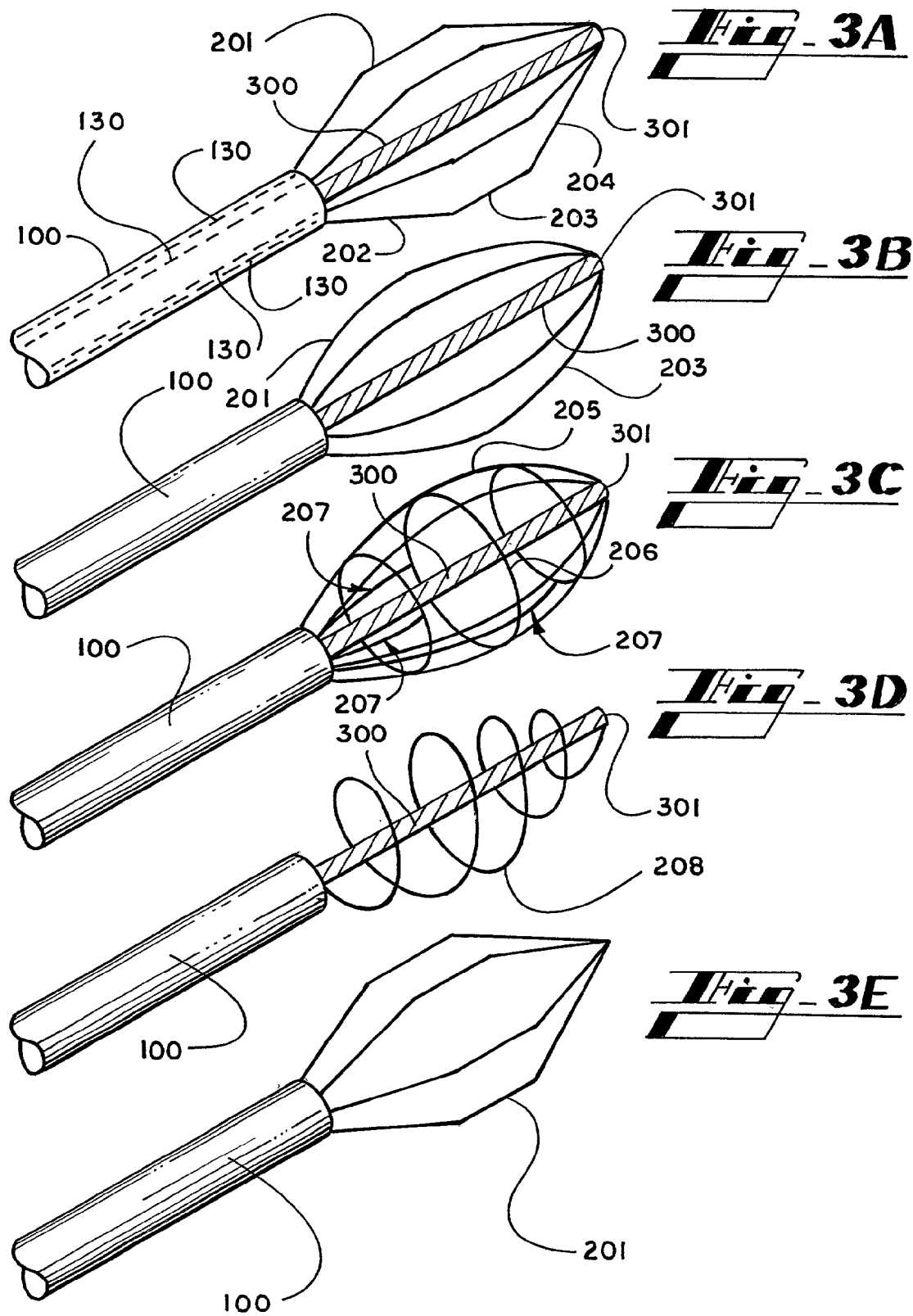

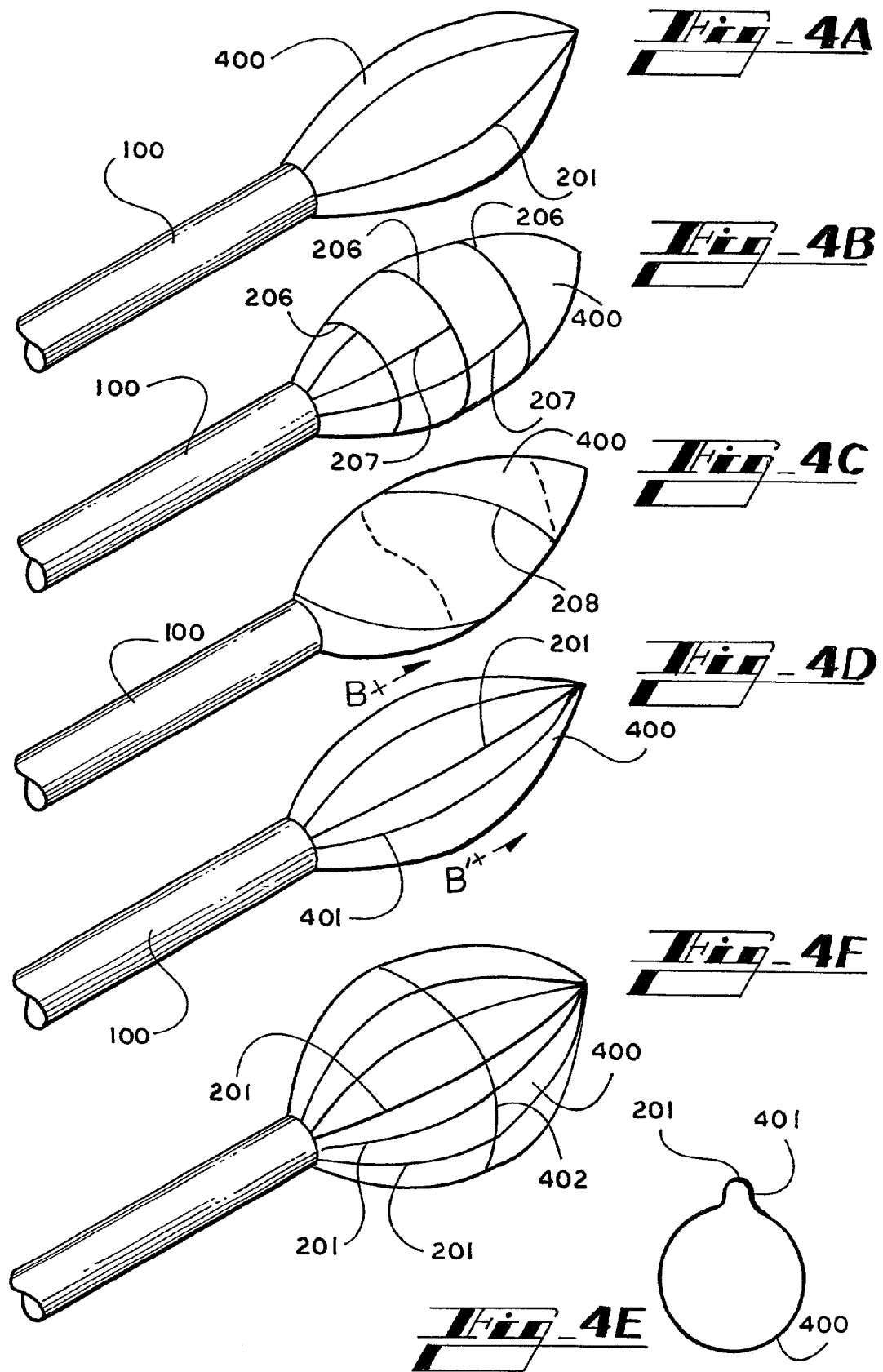

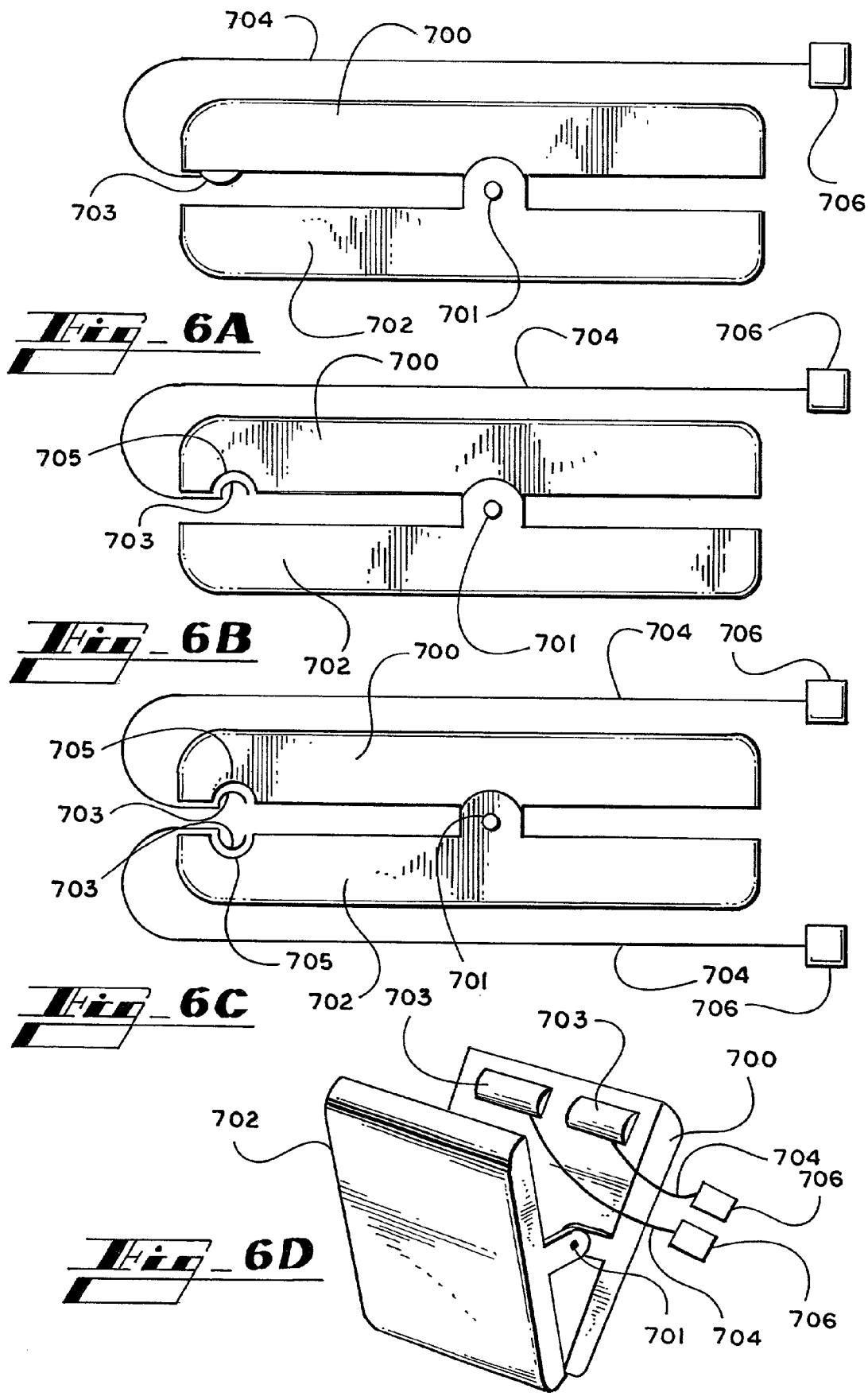

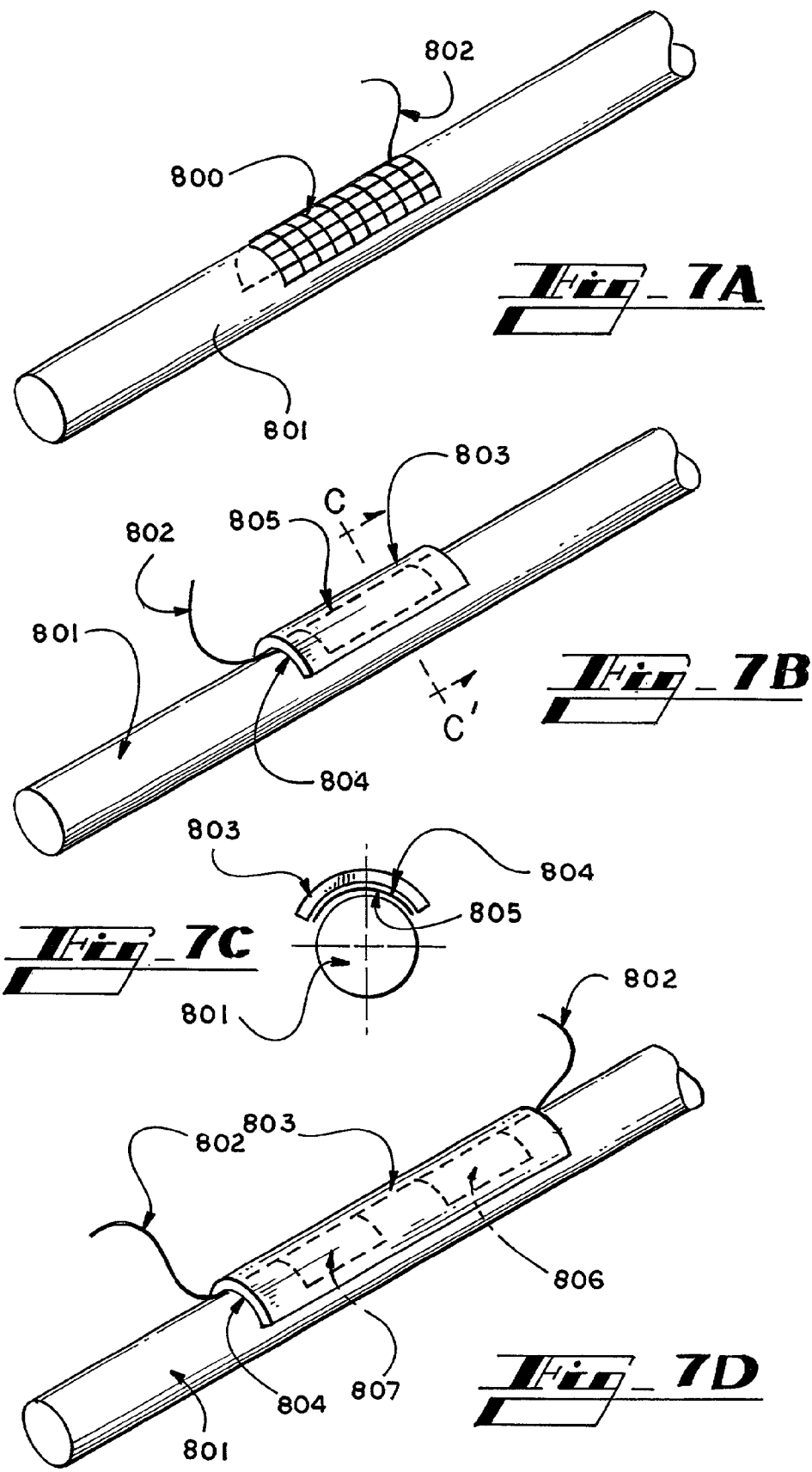

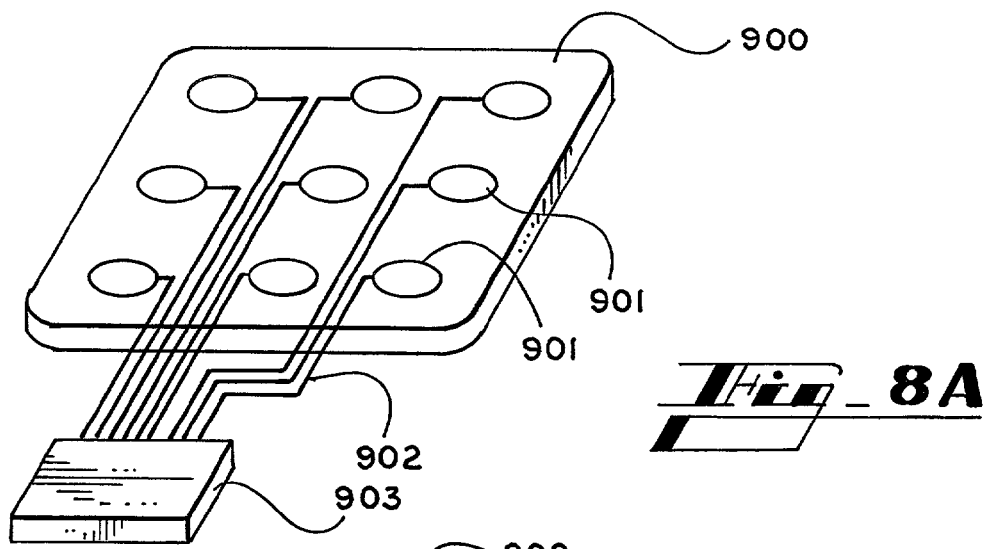
Fig_8A
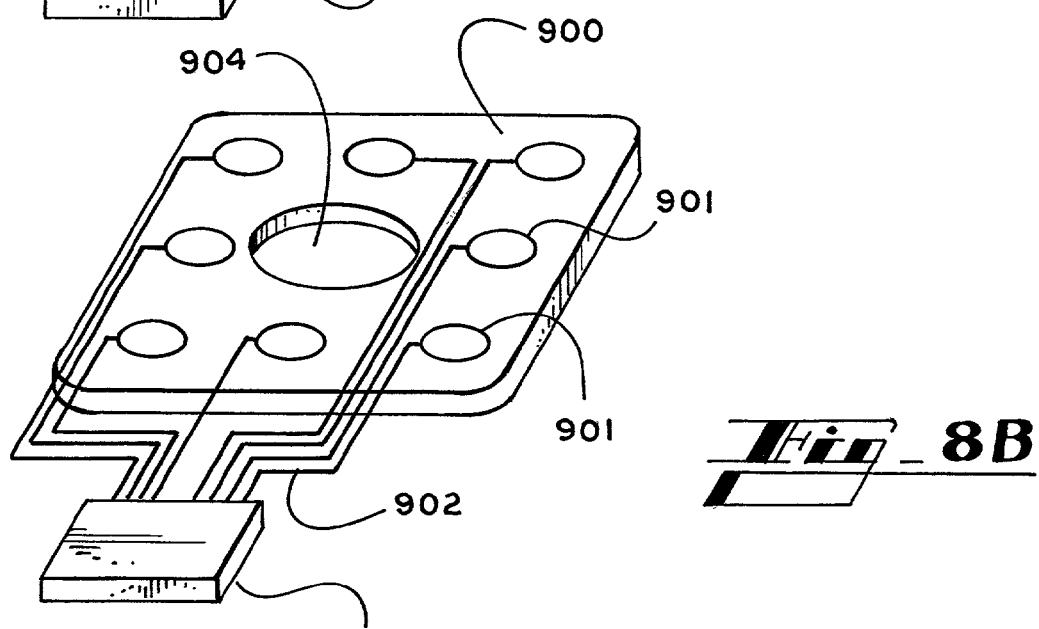
Fig_8B
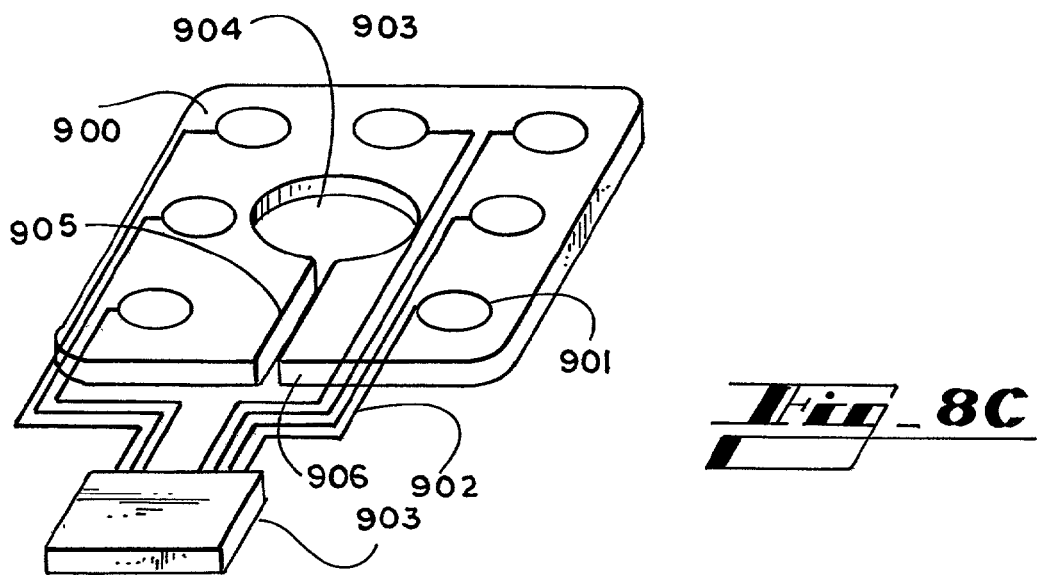
Fig_8C

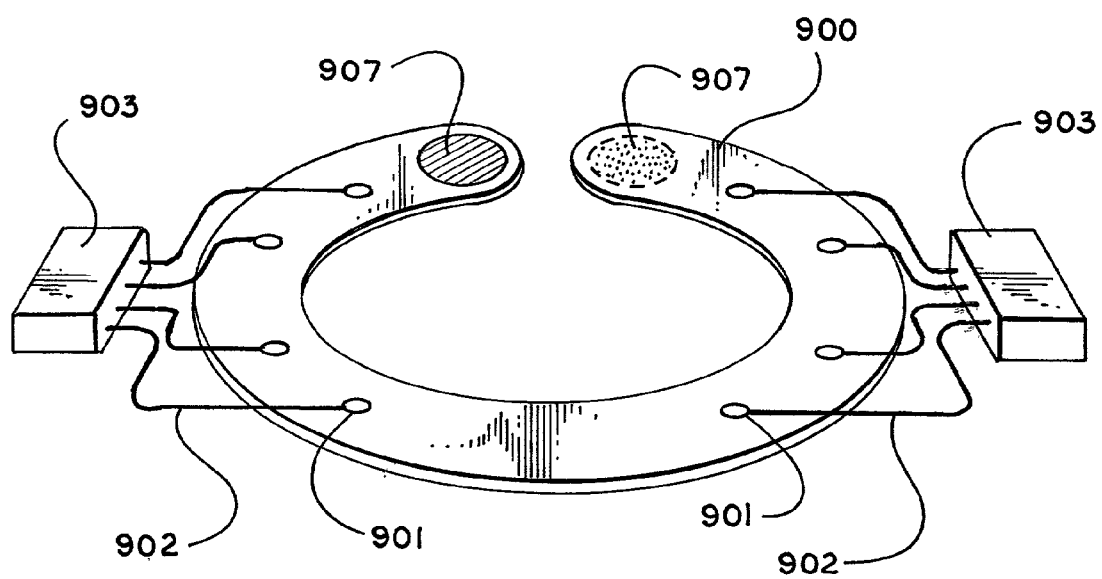
Fig_8D
Fig_8E
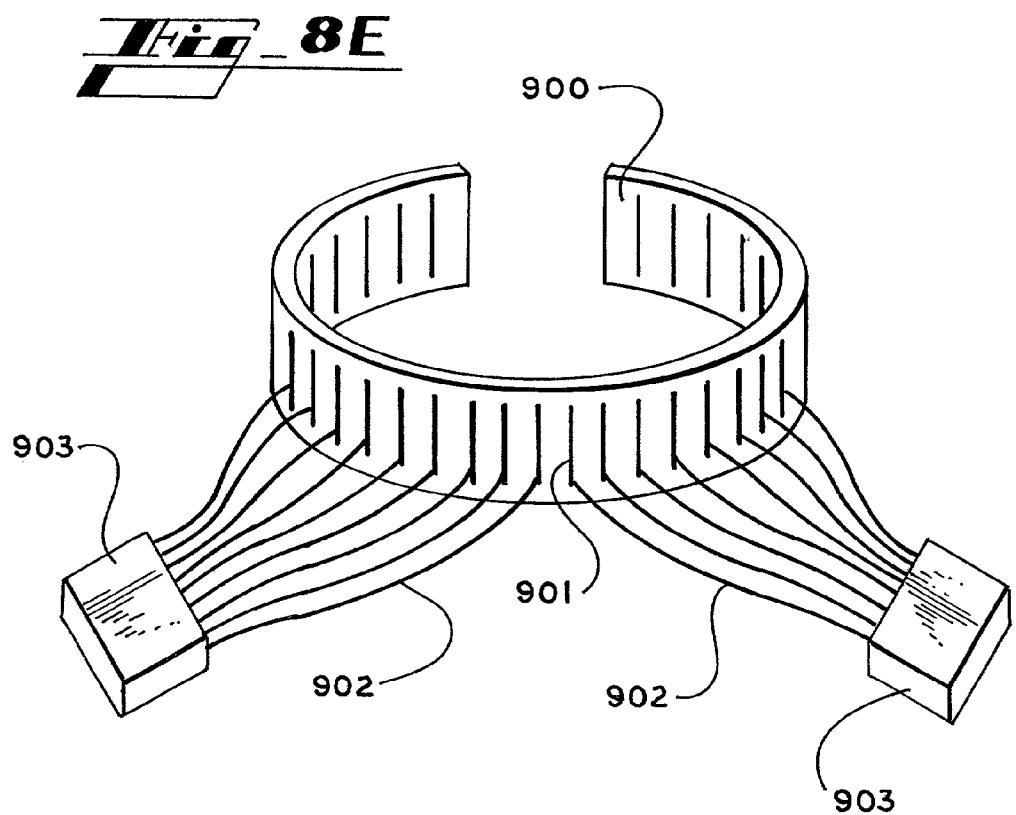

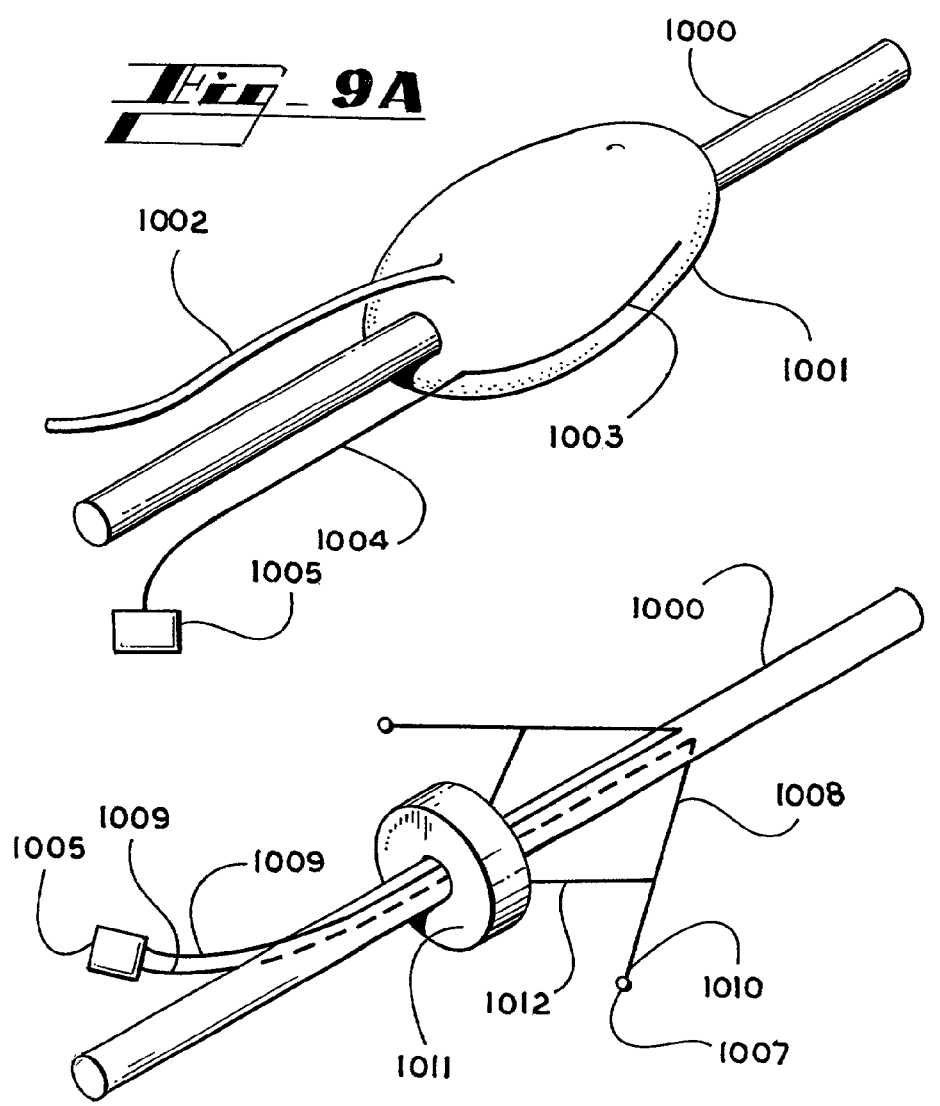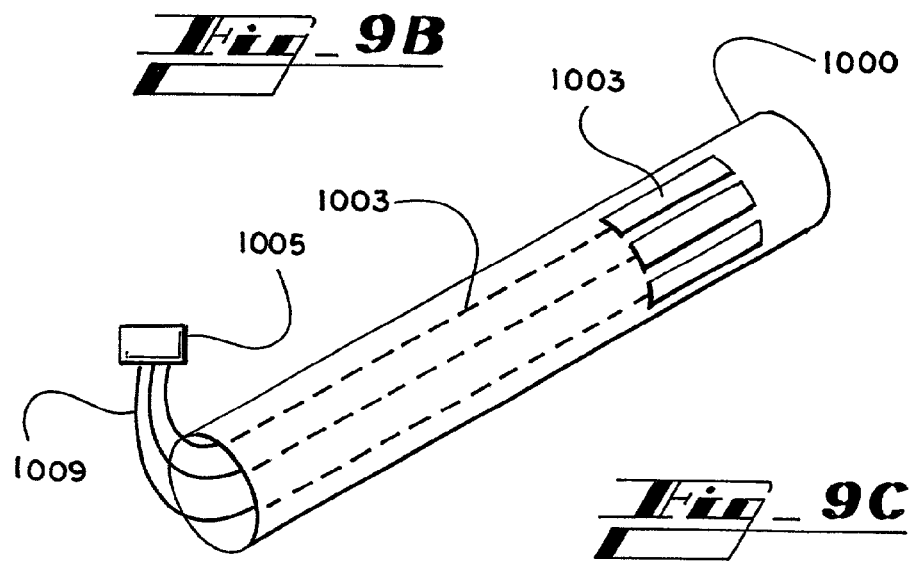

DEVICES AND METHODS FOR VAGUS NERVE STIMULATION

CROSS-REFERENCE TO RELATED APPLICATIONS

The present application is a continuation of non-provisional U.S. patent application Ser. No. 09/980,421, filed Apr. 23, 2002, which claims priority of PCT Application No. PCT/US00/17222 filed Jun. 23, 2000, and provisional U.S. Patent Application No. 60/141,202 filed Jun. 25, 1999.

TECHNICAL FIELD

The present invention relates to apparatus and methods for electrically-induced and pharmaceutically prolonged cardiac asystole. The present invention is useful for controlling heart beats and escape from asystole during cardiac surgery. The present invention is particularly useful during coronary by-pass surgery when anastomatic formation is readily disrupted by a beating heart.

BACKGROUND OF THE INVENTION

Cardiopulmonary bypass (CPB) and chemical arrest using cardioplegic solutions have traditionally provided surgeons with optimal operative conditions: hemodynamic control and cardiac quiescence. This optimal field has contributed to technical success in increasingly complex cardiac surgical operations. However, there has been recent interest in performing coronary artery bypass surgery without either cardiopulmonary bypass or cardioplegia. The quality of the distal anastomoses is a primary concern among cardiac surgeons who observe and perform coronary artery bypass graft procedures (CABG) unaided by cardiopulmonary bypass or cardioplegic arrest. Coronary artery bypass graft failure rate reported with off-pump coronary grafting range from 3.8–8.9%, while traditional CABG on CPB has a reported anastomotic failure rate of less than 1%. This may reflect a difference in anastomotic precision between off-pump CABG and CPB-aided CABG. Although the benefits of avoiding extra-corporeal circulation and global cardioplegia in beating heart procedures are important, they do not outweigh the performance of optimal coronary anastomoses.

The key difference in the anastomotic results between conventional CABG and off-pump CABG (OPCAB) is related to achieving elective asystole during construction of the distal anastomoses. Cardiac motion can be minimized during OPCAB procedures by inducing pharmacological bradycardia by administering beta adrenergic receptor blockers and mechanical stabilization by a variety of devices. Although these techniques improve operative conditions they only approximate the advantages of elective asystole that can be achieved with CPB and cardioplegia.

A state of Controlled Intermittent Asystole (CIA) would provide brief intervals of cardiac quiescence to facilitate placement of coronary anastomatic structures while avoiding the necessity of a cardiopulmonary bypass and cardioplegia. CIA would thus provide the surgeon with an important advantage otherwise gained only by full cardioplegic arrest on CPB. The CIA technique improves the precision of coronary anastomoses that would otherwise be performed on a beating heart and may reduce graft failure while increasing ease of operation, as described in application WO9909973, incorporated by reference herein in its entirety.

In particular, CIA can be achieved using unilateral (or bilateral) vagus nerve stimulation coupled with pharmacological potentiation of vagal impulses and pharmacological suppression of electromechanical escape activity. It has previously been demonstrated in WO 9817680, incorporated herein by reference in its entirety, that elective Controlled Intermittent Asystole is possible by vagus nerve stimulation after treatment with an acetylcholinesterase inhibitor, a beta-adrenergic receptor blocker, and a calcium channel blocker or combinations thereof. What is required, however, is an integrated system and apparatus that will provide optimal electrical pulses to the vagus nerve to induce cardiac arrest. The intermittent cardiac quiescent periods will be of sufficient duration to allow precise performance of surgical procedures that are not adversely interrupted by escape beats breaking through asystole. What are also required are electrostimulation devices that will permit the identification of the optimal position of an electrode or series of electrodes relative to a vagus nerve to induce asystole. What is further required are means and methods for applying the electric pulse to the nerve, either directly or indirectly and to administer a pharmaceutical composition to potentiate the influence of vagal stimulation on the heart rate, and prolong the period of asystole, thereby increasing the likelihood that the surgical procedure will proceed uninterrupted.

The present invention introduces apparatus, devices and methods that will allow the CIA technique to be performed with ease and precision.

SUMMARY OF THE INVENTION

The present invention solves the problems described above by providing a convenient apparatus for the application of an electrical pulse to the vagus nerve so as to arrest the heart beat in preparation for diagnostic or therapeutic medical or surgical procedures such as cardiac surgery. The apparatus directs an electrical pulse of optimized intensity and duration at a selected position along the nerve, and thereby induces cardiac quiescence. Spontaneous escape from asystole is prevented pharmacologically. The present invention, therefore, provides the apparatus and methods for the cardiac surgeon to induce a state of Controlled Intermittent Asystole (CIA), thereby greatly easing bypass surgery, significantly improving surgical quality and patient outcome.

The apparatus of the present invention allows the determination of the optimum location for an electrode to apply an electric stimulus to the vagus nerve. The apparatus correlates the response of the heart to the electrical pulse and modifies the stimulus to achieve suppression of the heart beat and then administers an optimized electric pulse to the vagus nerve. Both for safety and to deliberately terminate asystole once the surgical procedure in the heart is completed, the apparatus includes a cardiac pacer to stimulate the heart to escape asystole when this is desired.

The apparatus includes a multi-channel output means with at least one electrode linked to an electric pulse generator, and which will direct the electric pulse to the vagus nerve with efficiency and with minimal damage to the neural tissue. The electrodes are adjustable as to where they may be placed relative to the vagus nerve and offer various degrees of invasiveness. The electrodes of the present invention offer adaptability to the needs of the surgeon, variations in patient anatomy or physiology and the requirements of the cardiac surgical procedures being employed.

Accordingly, an object of the present invention is to provide an apparatus that will permit the surgeon to apply a selected electric pulse stimulus to the vagus nerve so that asystole will be induced.

It is a further object of the present invention to provide an apparatus that optimizes the electrical stimulus to the vagus nerve.

It is yet a further object of the present invention to provide electrodes for the direct or indirect application of an electrical stimulus to the vagus nerve that minimizes damage to tissue while allowing the surgeon to determine the optimal location for the electrode.

Yet another object of the present invention is to provide methods for the administering of an electrical stimulus to the vagus nerve and a pharmaceutical composition that will result in Controlled Intermittent Asystole.

An advantage of the present invention is that it offers the surgeon an apparatus that integrates the means to electrically stimulate the vagus nerve with the means to determine whether the heart beat is suppressed and will automatically determine the optimum stimulation to the nerve.

Another advantage of the present invention is the induction of a readily regulated and reliable state of asystole, greatly easing cardiac surgical procedures and comfort to the patient.

These and other features, objects and advantages of the invention and preferred embodiments of the present invention will become apparent from the detailed description that follows.

BRIEF DESCRIPTION OF THE DRAWINGS

FIG. 1 is a schematic arrangement of the vagus nerve stimulator. All of the components of the stimulator are shown as separate entities although it is envisaged that the interrogator, logic circuitry, the pulse generator, the cardiac monitor and the cardiac pacer could be incorporated and integrated electrically and electronically as a single unit in any combination.

FIG. 2A shows a longitudinal section through an embodiment of the catheter wire or basket electrode device. FIG. 2B shows a transverse section through the catheter device at the plane A–A' of FIG. 2A.

FIG. 3 shows embodiments of catheter wire or basket electrode devices. FIG. 3A shows a wire electrode. FIG. 3B shows a wire electrode with arcuate ribs. FIG. 3C shows a wire or basket electrode with circumferentially arranged electrodes disposed on longitudinal non-conductive ribs. FIG. 3D shows a helical wire electrode. FIG. 3E shows a wire electrode wherein the expansion means is shape memory.

FIG. 4 shows embodiments of the inflatable balloon electrode device. FIG. 4A shows a balloon electrode with longitudinal electrodes. FIG. 4B shows a balloon electrode with circumferentially arranged electrodes. FIG. 4C shows a balloon electrode with a helical electrode. FIG. 4D shows a balloon electrode with a longitudinal electrode disposed on a longitudinal raised ridge. FIG. 4E shows a transverse section through the embodiment of FIG. 4D at the plane B–B'. FIG. 4F shows a balloon electrode with longitudinal electrodes not fixed to the surface of the balloon and united by a wire yoke.

FIGS. 6A–D show embodiments of the clip electrode device.

FIG. 7A shows a wire mesh neural electrode. FIG. 7B shows cuff neural electrode conforming to the shape of the nerve. FIG. 7C shows a transverse section through the cuff electrode at plane C–C'. FIG. 7D shows a cuff neural electrode with two separate electrodes.

FIG. 8A shows a pad embodiment of cutaneous electrode array. FIG. 8B shows a pad electrode with traversing hole to surround the neck. FIG. 8C shows an electrode with traversing hole to surround the neck. FIG. 8D shows a cutaneous electrode in a necklace configuration. FIG. 8E shows a cutaneous electrode in a turtleneck configuration.

FIG. 9A shows a tube balloon electrode device for insertion into the trachea or esophagus. FIG. 9B shows a tube umbrella electrode device. FIG. 9C shows an alternate electrode device of the present invention.

DETAILED DESCRIPTION OF THE DISCLOSED EMBODIMENT

Figure 5A:
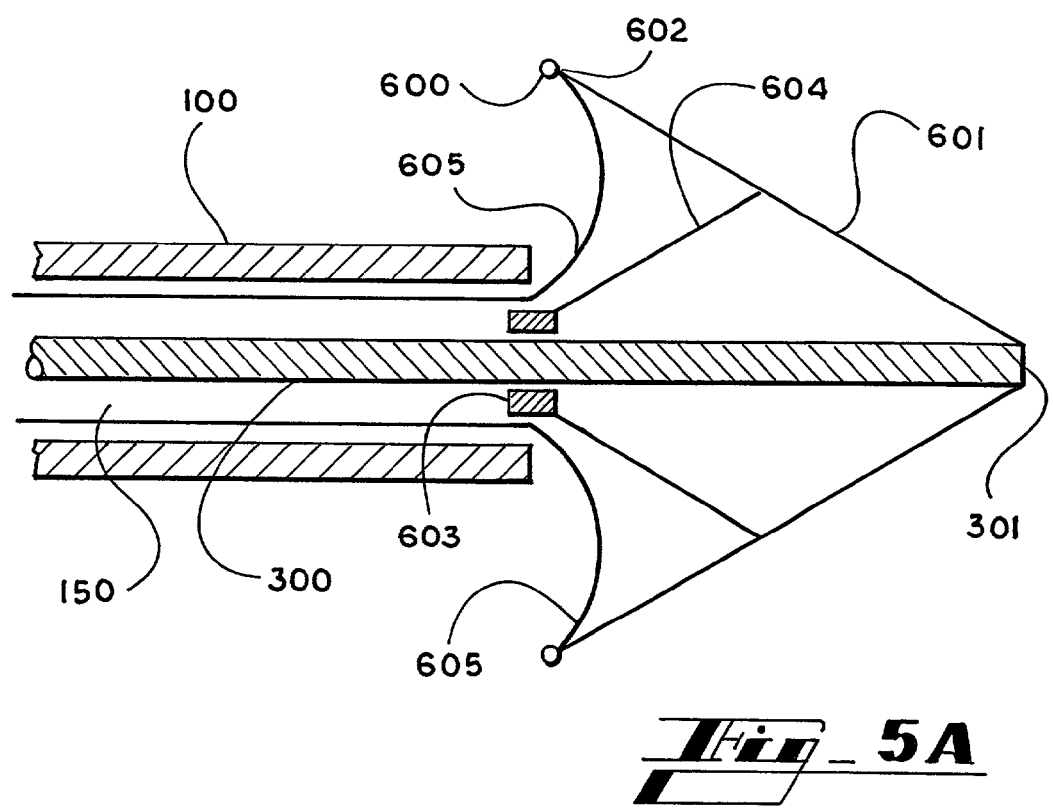
FIGS. 5A and B show longitudinal sections through a catheter umbrella electrode device.

The present invention provides devices and methods for achieving Controlled Intermittent Asystole by means of vagus nerve stimulation. While the purpose of the devices is for achieving Controlled Intermittent Asystole status by means of vagus nerve stimulation, the devices are not limited thereto, and it will be recognized that various embodiments of the invention can be used to facilitate other medical or surgical procedures.

The present invention provides apparatus for the regulated electrostimulation of the vagus nerve to induce a state of asystole. The embodiments of the vagal nerve stimulator apparatus also include electrodes, catheters and electrode catheters suitable for applying a selected electrical pulse to the vagus nerve for the purpose of controlling cardiac rhythm. The apparatus include a pulse generator, a cardiac pacer and a cardiac monitoring means. The apparatus further comprises interrogative electronic circuitry and computer readable software intended that will allow the apparatus to determine the optimal position of an electrode for the delivery of an effective amount of neural electrostimulation to arrest the beating heart. The apparatus of the present invention also includes a cardiac stimulator and control circulatory and switches to revive the heart.

The present invention also provides methods for the induction of Controlled Intermittent Asystole (CIA) by means of the co-administration of an effective amount of a pharmaceutical composition comprising an acetylcholinesterase inhibitor, a beta-adrenergic blocker and a calcium channel blocker and the electrostimulatory impulse that will arrest cardiac activity.

Definitions

The term "electrode" is used herein to mean any conductor used to establish electrical contact with an area of a human. Said area may be, but is not limited to, the surface of the skin, the interior surface of a blood vessel, the gastroentological tract, the respiratory tract, or any other internal or external surface of the anatomy.

The term "cardiac monitoring means" is used herein to mean any device that will measure the frequency or amplitude of the output of the heart. The output parameters include, but are not limited to, the electrical output of the heart, the pulse strength or its frequency, or systolic or diastolic blood pressure. The "cardiac monitoring means" can be, but is not limited to, an electrocardiograph, a sphyngometer, a pulse detector or any other mechanical, electric or electronic device known to one of skill in the art that will detect cardiac activity and translate said activity measurement to an electrical signal.

The term "cardiac pacer" is used herein to mean any device that will induce the heart to beat in a regular or intermittent manner.

The term "electric pulse" is used herein, but is not limited to, a unipolar or bipolar pulse, wherein the unipolar pulse is between a single electrode implanted in, or situated on, a patient, and an electrode electrically connected to the ground and wherein the bipolar pulse is between at least a pair of electrodes in or on the patient, with no electrode being directly grounded.

The terms "electric pulse generator" and "pulse generator" are used herein to mean any device or devices that will deliver an electric pulse of preselected frequency and amplitude. The device will include electronic circuitry electrically linked to variable switch means to regulate output voltage, frequency and amplitude of the current supplied.

The term "means of supplying an electric pulse" is used herein to mean, but is not limited to an electrically conductive wire, strip or other means known to one of skill in the art, that is electrically connected at one end to a source of electricity and at the other end to the site of delivery of the electricity, such as, but not limited to, an electrode.

The terms "interrogator", 'interrogative device" or "interrogative circuitry" are used herein to mean any computer or electronic circuitry or device, including computer readable software, that will receive the signal for a cardiac monitoring means and adjust the electric pulse delivered by the pulse generator until the cardiac activity is temporarily, substantially or completely eliminated. The "interrogator" will also include circuitry to sequentially assign an output pulse from the pulse generator to at least one electrode of a plurality of electrodes. The interrogator also includes a logic circuit wherein it may integrate the cardiac monitoring means output, the pulse generator and the selected electrode. The pacer also, but not necessarily is electrically linked to the interrogator. The interrogator may be microprocessor based and include software to compare the signal from a cardiac monitoring means and regulate the output of the pulse generator and the cardiac pacer.

The term "catheter" is used herein to mean any tube device that can be introduced into the body of a patient or animal through an orifice or incision thereof. The device includes, but is not limited to, an intravascular catheter, a tracheal catheter or tube, a nasogastric or esophageal tube or catheter or any other tube device that may be introduced into a human or animal.

The term "manual switch" or "manually operable switch" is used herein to mean any switch device operable by foot, hand, voice, or any other means available to the surgeon during the course of surgery and that will override or supplement on automatic switch means such as but not limited to that provides by the interrogator unit.

Pharmaceutical Compositions

The terms "pharmaceutical Controlled Intermittent Asystole composition" or "CIA composition" are used herein to include, but are not limited to, pharmaceutical compositions capable of prolonging a state of cardiac asystole. The pharmaceutical compositions comprise an acetylcholinesterase inhibitor selected from, but not limited to, donepezil hydrochloride, tacrine hydrochloride, pyridostigmine bromide, neostigmine methylsulfate, edrophonium chloride, physostigmine salicylate, a β-adrenegic, receptor inhibitor selected from, but not limited to, sotalol hydrochloride, timolol maleate, esmotol hydrochloride, carteolol hydrochloride, propranolol hydrochloride, betaxolol hydrochloride, penbutolol sulfate, metoprolol tartrate, acebutolol hydrochloride, atenolol, metoprolol succinate, bisoprolol fumarate, and a calcium channel blocker selected from, but not limited to, nifedipine, verapamil hydrochloride, nicardipine hydrochloride, diltiazem hydrochloride, isradipine, nimodipine, amlodipine besylate, felodipine, nifedipine, nisoldipine, and bepridil hydrochloride. In a preferred embodiment, the composition comprises an acetylcholinesterase inhibitor, a beta-adrenergic receptor inhibitor and a calcium channel blocker. In a more preferred embodiment of the present invention the composition comprises between about 0.1 mg/kg body weight to about 100 mg/kg body weight of pyridostigmine, 0.01 mg/kg body weight to about 100 mg/kg body weight of propanolol hydrochloride and between 0.001 mg/kg body weight and 1.0 mg/kg body weight of verapamil hydrochloride. Most preferably the pharmaceutical composition comprises 500 μg/kg body weight of pyridostigmine, 80 μg/kg body weight of propanolol hydrochloride and 50 μg/kg body weight of verapamil hydrochloride.

The preferred method of administering the CIA composition to achieve CIA is as a slow bolus delivered intravenously over a 1–10 minute period. The CIA composition is given to establish a pharmacological background state in which subsequent vagus nerve electrostimulation causes CIA. The CIA composition may be maintained at effective blood concentrations in a human patient by slow continuous or intermittent infusion. Repeated bolus administration may be necessary in some patients. The effects of the CIA composition may be reversed chemically if necessary by intravenous administration of a drug chosen from, but not limited to, atropine sulfate, isoproterenol hydrochloride, and epinephrine hydrochloride.

Abbreviations

The following abbreviations are used in this description. CIA designates Controlled Intermittent Asystole. CABG designates Coronary Artery Bypass Grafting. CPB designates Cardiopulmonary Bypass. OPCAB designates Off Pump Coronary Artery Bypass Grafting, or coronary grafting without the use of cardiopulmonary bypass, synonymous with beating heart bypass surgery. MIDCAB designates Minimally Invasive Direct Coronary Artery Bypass Grafting, an off-pump grafting procedure, typically performed through a left thoracotomy. E-CABG designates Endoscopic Coronary Artery Bypass Grafting, i.e. CABG performed using endoscopic instruments inserted through small intercostal incisions, and in the absence of a sternotomy or formal thoracotomy. All embodiments of the invention may be used with pump-assisted or entirely off-pump procedures.

Controlled intermittent asystole can be achieved by potentiation of vagal induced bradycardia by means of a pharmacological combination. The chronotropic effect of vagal nerve stimulation in the absence of pharmacological potentiation includes a very brief initial pause followed by "vagal escape" beats and transient bradycardia. Vagus nerve stimulation alone does not produce controlled asystole. On the other hand, increased acetylcholine activity resulting from acetylcholinesterase inhibition, the prevention of electromechanical escape from asystole by beta-adrenergic receptor and calcium channel blockade, and the application of simultaneous vagal stimulation produces a marked potentiation of vagal-induced asystole, and a means of achieving Controlled Intermittent Asystole (CIA). CIA can, therefore, be reproducibly achieved for prolonged periods, or for multiple shorter sequential intervals selected as appropriate for the construction of coronary anastomoses, or other medical or surgical purposes.

It has unexpectedly been found that stimulation of the right vagus nerve combined with administration of the preferred pharmacological composition results in prolonged asystole. While electrical stimulation of the right vagus nerve is preferred, electrostimulation may also be effectively applied to the left vagus nerve or to both nerves simultaneously or sequentially. The site of nerve stimulation can be, but not necessarily, in the neck.

The preferred indirect method and site of stimulation of the vagus nerve is by means of a percutaneous catheter or electrode probe implanted in the internal jugular vein, trachea, esophagus, or a combination thereof. Other preferred locations for vagus nerve stimulation include, but are not limited to, of the right or left vagus nerve or both. The nerve may be stimulated by unipolar excitation, wherein the ground electrode is located at the skin surface, or by direct or indirect bipolar excitation. An internal jugular vein stimulating electrode device can be introduced through the sternotomy via the right atrium, the right atrial appendage, the inferior vena cava or the superior vena cava. It can be associated with a flow-through cannula, for the purpose of administrating fluids or drugs. A stimulating electrode may also be placed in direct contact with the vagus nerve by thoracoscopy, thoracotomy or sternotomy and during the course of open-chest thoracic surgery. The present invention contemplates the use of any of the presently described devices with the methods for achieving controlled intermittent asystole, including the use of pharmaceutical compositions for achieving the same.

The present invention contemplates implantable catheters having a plurality of electrodes. An electric pulse can be sent to a single electrode or to at least two electrodes randomly or non-randomly selected, either manually or electrically, by an interrogator device. The interrogator device will measure cardiac output and determine cardiac activity as a function of the electrode or electrodes used. A plurality of electrodes on an intravascular catheter will allow the surgeon to determine which electrode or electrodes stimulate the vagus nerve to achieve maximum suppression of cardiac activity.

While the optimal number of wires can vary depending upon the circumstances, four, eight or twelve wires per basket provide symmetry. Each wire is an independent electrode, electrically exposed only on its outer service at the point where it makes contact with the wall of the internal jugular vein, trachea, or esophagus. The electrodes may be self-expanding or retractable as a group when the device is deployed.

The vagus nerve can be stimulated in a unipolar or bipolar fashion. An array of electrodes in the form of a basket, balloon or umbrella device can be used to stimulate the vagus nerve between a chosen electrode rib and a separate ground, or between two chosen electrode ribs on the same device. This applies the basket, balloon or umbrella devices, whether with strips of foil, wires or umbrella tip electrodes, and regardless of whether the strip or wire electrodes are oriented longitudinally, transversely or spirally. For unipolar excitation, the ground can be an adhesive pad fixed to the patient's skin, either overlaying the vagus nerve or placed elsewhere.

The vagus nerve may be most effectively and easily stimulated with a single basket or balloon or steerable wire device in the internal jugular vein, esophagus or trachea. Alternatively, a bipolar electric field may be used that is preferably, but not limited to, between electrodes on individual devices in separate anatomical structures. For example, a balloon, basket or umbrella catheter may be in the internal jugular vein, while another electrode is on a balloon, basket or umbrella in the trachea or in the esophagus.

Endotracheal and endoesophageal balloons, umbrellas or basket electrodes can be fitted on standard endotracheal or nasogastric tubes and nasogastric tubes. In the balloon device, electrically conductive electrodes can be oriented longitudinally, circumferentially, or helically, relative to the longitudinal axis of the anatomical feature in which the electrode device is implanted. In either longitudinal or circumferential embodiments, electrically active strips can be continuous or interrupted. In the case of interrupted strips, each segment of the strip can be an independent electrode.

Any two independent electrodes can be used in a bipolar fashion. Each independent electrode is an option recognized by a logic and control software of a multi-channel control box device. In the case of catheters bearing balloon, basket, or umbrella electrodes, two electrodes on catheters in distinct anatomical structures can be inflated or deployed adjacent to each other. This arrangement will gently place the vagus nerve between two electrode strips, and capturing the vagus nerve with the smallest possible effective voltage.

The optimum electric field may be between two electrically independent strips of a single catheter device in a single anatomic structure such as, but not limited to, the internal jugular vein. Alternatively, and depending on individual patient variability, it may be that optimal pacing is achieved between strips on two different catheter devices, each in a different anatomical structure. Such paired locations for the electrodes would include, but is not limited to, the jugular vein and esophagus, jugular vein and trachea or the esophagus and trachea. In each of these embodiments, the catheter devices are preferably positioned by the surgeon following ultrasound guidance, direct palpation, measurements of catheter insertion length, or any combination thereof. Fluoroscopy and echocardiography are alternative technologies that can be applied to confirm positioning.

At least one electrode can be applied directly to a surgically exposed vagus nerve. Thoroscopy, thoracotomy, or sternotomy can access the nerve itself. The present invention provides electrode devices that may be directly attached to the vagus nerve with greatly reduced mechanical damage to the neural tissue. This represents a significant advantage since repositioning of the electrode and therefore repeated clamping to the nerve may be necessary to determine the optimum location for electrical induction of asystole.

Direct placement of an electrode onto a vagus nerve can be by a clip means that carries at least one electrode, or a cuff means that completely or partially envelopes the nerve. The cuff may comprise solely an electrode means or the at least one electrode that is held against the nerve by the cuff means. The electrodes are comprised of material that is compressible or otherwise shaped to avoid indenting or crushing the neural tissue.

An entirely cutaneous array of adhesive electrodes can alternatively be used to create an electric field that would "capture" and stimulate the vagus nerve. Such an array can consist of, but is not limited to, an adhesive pad with from 1 to about 100 electrically independent skin electrodes, each isolated from the others and electrically connected to a multi-channel connector or hub. A single selected electrode from an array can be used for unipolar stimulation. Alternatively, they may be employed in pairs or other multipolar electrode combinations, or in combination with at least one other electrode positioned in the internal jugular vein, trachea or esophagus for bipolar stimulation.

The methods of the present invention introduce an electrode to a vagus nerve and thereby apply an electrical stimulation that results in a transient cardiac quiescence. The electrode device may be repositioned by the surgeon to a more advantageous location resulting in a greater desired cardiac response. Alternatively, one or more of the electrodes of the device may transmit an electric pulse to the nerve. The apparatus of the present invention will self-determine the preferred electrical charge to apply and to which electrodes. The method of the present invention will further comprise administering a pharmaceutical composition that will suppress escape of the heart from asystole. This will relieve the surgeon of concern that the quiescent heart will re-enter brachycardia or full beat while in the midst of a surgical procedure such as the suturing of an anastomosis between a bypass graft and a coronary artery.

The present invention is further illustrated by the following examples, which are not to be construed in any way as imposing limitation upon the scope thereof. On the contrary, it is to be clearly understood that resort may be had to various other embodiments, modifications and equivalents, thereof, which, after reading the description herein, may suggest themselves to those skilled in the art without departing from the spirit of the present invention.

Vagal Nerve Stimulator Apparatus.

The present invention, as shown in FIG. 1, provides a multi-channel interrogator device box 10 that is microprocessor based and includes logic and control software to interrogate the closest electrode or electrode pairs to the vagus nerve "blindly" and automatically. This electronic device receives continuous input from a cardiac monitoring device 20 operably connected to a patient by a connection means 21. The device can then sample the induced cardiac response resulting from an electric pulse applied to a particular electrode 30 or electrode pair 31 and thereby identify the electrode 30 or electrode pair 31 that are the most effective in producing Controlled Intermittent Asystole. Thus, the surgeon and anesthesiologist can be relieved of the necessity of physically locating the vagus nerve, as well as having to directly map the stimulation.

The multi-channel interrogator device box 10 automatically selects the most appropriate electrode or electrodes of an array of electrodes as a function of the cardiac output response. Although the logic and control software, however, is conceived to automatically interrogate the available electrode combinations, it is important that this multi-channel apparatus also be able to selectively function in a manual mode. The apparatus will, therefore, have a display, a plurality of numeric keys and knob dials 11, a vagus nerve stimulation switch, and a vagus nerve destimulation switch, that can independently access the various electrodes electrically connected to a patient, such that an electrode 30 or electrode combination 31 can be manually selected.

The apparatus of the present invention further comprises a pulse generator 40 such as, but not limited to, GRASS™ nerve stimulator units. Such an electrostimulator includes, but is not limited to, a regulated power source, such as a battery and regulator, a nerve stimulation timer circuit, a nerve destimulation timer circuit, and a power amplifier(s). The type and quantity of timer circuits and power amplifiers can be chosen from any known to one of skill in the art.

The apparatus of the present invention offers a wide variety of unipolar or bipolar outputs 41. The pulse generator 40 allows the duration of impulse to be controlled by a foot switch 50. Impulse parameters can be varied either manually or automatically. Available frequencies can range between about 1 Hz and about 500 Hz. Preferred pulse amplitudes are in the range from about 0.1 volt to about 100 volts, with amperage of from about 0.05 mA to about 50 mA.

The apparatus of the present invention further comprises a cardiac pacer device 60 for pacing the heart out of asystole and a pacer-to-patient connecting means 61. In a preferred embodiment the cardiac pacer 60 is electrically connected to the logic and control circuit and associated software so that it is integrated with the pulse generator for vagal nerve stimulation.

The vagal nerve stimulator output can be slaved to the cardiac pacemaker, which can have parameters similar to those of presently available pacer devices. The cardiac pacer output can be "off" whenever the vagal stimulator output is "on". The software controlling the cardiac pacer and vagal stimulator can automatically commence cardiac pacing if the heart does not resume beating within a predetermined interval from cessation of vagal nerve electrostimulation. This feedback mechanism provides a significant safety feature when CIA is used clinically.

In another preferred embodiment of the present invention, a foot pedal assembly 50 can activate the vagus nerve stimulator. A foot pedal assembly 50 has a normally open heart stimulation foot switch and a heart destimulation foot switch that can be used as an alternative to either automatic or hand-operated switches. The provision of a foot pedal assembly 50 permits the surgeon to control when the heart and vagus nerve stimulation and destimulation occur while leaving the hands free to perform other procedures. This also permits the surgeon's hands to remain sterile, since contact with the housing or switches is avoided. The foot pedal assembly 50 is connected via cable or other means to an electronic control device within the housing.

During open chest surgery or minimally invasive surgery, the foot switch is pressed to selectively initiate or stop the heart beat as required. The heart may be stimulated either through the present device to beat for a predetermined time to permit blood flow throughout the body and then again be electrostimulated via the vagus nerve for asystole and allow the surgeon to continue stitching. An alternative to providing two different foot pedal assemblies 50 would be to provide a single foot switch with intermittent switches between stimulation and destimulation each time the switch is actuated. It is also contemplated that automatic stimulation by means of a cardiac pacer device could be provided after a preset time period.

In yet another embodiment of the invention, a voice-activated switch can be used that incorporates commercially available voice-recognition software into a verbal control mechanism to turn the vagal nerve stimulator on and off. This switch can also function in a "slaved" fashion, such that whenever the vagus nerve stimulator is turned on, output from the cardiac pacemaker is turned off. While these hardware devices are modifications of presently available devices, they would be customized and combined into a single unit for this new application of producing controlled intermittent asystole.

Intravascular Catheter Electrode.

The present invention provides intravenous catheters having a distally disposed electrode means that can be expanded in the internal jugular vein so as to press up against the internal wall of the internal jugular vein and force contact between an electrode and the blood vessel wall. This allows electric current and electric fields to pass through the thin wall of the internal jugular vein to stimulate the vagus nerve, which lies immediately adjacent to the internal jugular vein. The electrode means can be added to any intravascular catheter device known to one of skill in the art including, but not limited to, the Swan Ganz catheter, the tip of which would aid in proper catheter positioning and monitoring of pulmonary artery pressures. The catheter itself can also have one or move intravenous port(s) for administration of fluids and drugs, with appropriate intravenous access hubs. The electrical access to the electrode means can be provided via an external multi-channel electric plug connector.

The intravenous catheters can be steerable catheters that allow precise positioning of an electrode means close to the vagus nerve, thereby minimizing the electrical energy needed to "capture" the nerve and induce Controlled Intermittent Asystole. It is thereby possible to "map" the location of the vagus nerve by determining the feedback signal derived from the cardiac output monitor in response to nerve stimulation.

The present invention, as shown in FIGS. 2A and 2B, provides an intravascular catheter device for delivering an electric pulse to a nerve. The catheter device comprises a shaft 100 having a distal region 110 and a proximal region 120, the distal region 110 having an expandable electrode means 200 and an electrode expanding means 300. The shaft 100 may include a means of supplying an electrical pulse 130 to the expandable electrode means 200. The means of supplying an electrical pulse 130 are in electrical contact with a multi-channel connector means 131. The electrical pulse supply means 130 also has a hub 132 attached thereon to hold the supply means 130 firmly. The shaft 100 may further comprise a handle 101 and a transcutaneous sheath 102. The intravascular catheter can be inserted though said sheath 102, which can be sutured to a patient's skin near the site of insertion. There can be a valve on said sheath to avoid bleeding, and the catheter can be rotatable within the transcutaneous sheath 102. While not wishing to limit the invention, the preferable means of supplying an electrical pulse 130 to an electrode 200 is a wire.

Although it is contemplated that the dimensions of the expandable electrode means 200 will be selected as a function of the blood vessel or other anatomical structure receiving the catheter, and where the catheter is inserted into the recipient human or animal, in preferred embodiments of the electrode, the length of the electrode will be between about 1 cm and 15 cm, most preferably between about 2 cm and 6 cm. The diameter of the shaft is preferably between about 0.5 and 5 mm, most preferably 1 mm.

The preferred length of the intravascular catheter is dependent upon the point of insertion of the catheter into a human or animal. When the catheter is inserted in the neck, the length of the shaft 100 is between about 15 cm and 30 cm, preferably between about 15 cm and 25 cm. For subclavian insertion of a catheter, the preferred length of the shaft 100 is between about 20 cm and 40 cm, most preferably between about 25 cm and 35 cm. For femoral insertion of the catheter, the preferred length of the shaft 100 is between about 50 cm and about 120 cm, most preferably between about 80 cm and about 100 cm. For atrial insertion, wherein the catheter electrode device is advanced from the cardiac atrium into the superior vena cava or internal jugular vein, the preferred length is between about 5 cm and about 25 cm, most preferably between about 10 cm and 15 cm.

(i) Catheter Wire or Basket Electrode. The expanding electrode means 200 shown in FIG. 2A is selected from a variety of patterns and shapes that resemble, but are not necessarily limited to, the ribs or staves of a barrel, as shown in FIGS. 3A–3D. The electrode means are electrically independent of each other.

A preferred embodiment of the expandable electrode means 200 and the electrode expanding means 300 is shown in FIG. 3A, wherein the electrode means 200 is a basket catheter electrode with at least one expandable rib 201. In a preferred embodiment, the expandable rib 201 or plurality of such ribs are electrically conductive wires. Thin wires are preferred with a thickness of between about $1/128$ inch and $1/8$ inch, most preferably between about $1/64$ and $1/16$ inch. In another preferred embodiment, the expandable ribs 201 are electrically conductive strips from about $1/128$ inch to about $1/4$ inch wide, most preferably from about $1/64$ inch to $1/4$ inch. In yet another preferred embodiment the expandable ribs 201 are electrically non-conductive strips with electrodes dispersed thereon. In a most preferred embodiment, the electrically conductive wire or strip is comprised of a proximal region 202, a central region 203 and a distal region 204, wherein the proximal region 202 and the central region 203 form a first angle and the central region 203 and the distal region 204 form a second angle. Preferably the first and second angles are between about 1° and about 180°. Most preferably, the first and second angles are between about 90° and about 120°.

Preferably, the ribs 201 are between 1 and about 48 in number, more preferably between 2 and about 12 in number. In a preferred embodiment, the length of the expanded electrode 200 is between about 1 and about 15 cm. More preferably, the length is between about 2 and about 6 cm. The diameter of the catheter before expansion is the diameter of the catheter shaft 200 and is 0.5 mm to about 5 mm, most preferably 1 mm.

In one embodiment of the present invention, the central region 203 is electrically exposed, and the proximal region 202 and distal region 204 are electrically insulated. In this embodiment, the length of electrically exposed central region 203 is between 0.1 cm and about 10 cm, most preferably between 0.5 and about 5 cm. The means of applying an electrical pulse 130 are preferably, but not limited to, wires electrically connected to the expandable ribs 201. The wires 130 are electrically independent of one another, and pass through the shaft 100. The wires 130 and are electrically connected to a multi-channel electrical connection 131, as shown in FIG. 2A. The electrode expanding means of the preferred embodiment is a rod 300 capable of sliding within a lumen 150 of the shaft 100. The rod 300 has a distal end 301. The expandable ribs 201 are attached to the distal end 301 of the rod 300.

In another embodiment of the present invention, shown in FIG. 3B, the expandable ribs 201 are arcuate when expanded. In a preferred embodiment, the length of an electrically exposed central region 203 of the expanded arcuate electrode is between about 0.1 cm and about 2.5 cm. More preferably, the range is between 0.5 cm and 2.0 cm.

The present invention is intended to include other forms of the expandable electrode such as, but not limited to, electrodes 206 circumferentially disposed coaxially around the rod 300, shown in FIG. 3C, a helix as shown in FIG. 3D. In the circumferential electrode embodiment shown in FIG. 3C, non-conductive ribs 205 support electrically exposed electrodes 206 circumferentially disposed thereon. Each circular electrode 206 is electrically connected to an electric pulse applying means 207 and a multi-channel electrical connection 131, as shown in FIG. 2A.

The expandable catheter electrodes may be deployed, once the catheter has been implanted in the blood vessel and placed by the surgeon in the proximity of a vagus nerve. Expansion is by retracting the shaft 100 relative to the distal end 301 of the rod 300. This exposes the self-expanding electrode means 200 that were disposed against the rod 300 within the lumen 150 of the shaft 100. In another embodiment, the cathode means 200 can be fixed to the tip 301 and to the distal end 110 of the catheter shaft 100. In this embodiment, partial retraction of the rod 300 into the lumen 150 of shaft 100 will force the electrode means 200 to expand outwards. The electrode means 200 are stretched when the rod 300 is extended relative to the distal end 110 of the shaft 100, thereby reducing the diameter of the rod 300 and electrode 200, to facilitate catheter electrode insertion into, or removal from, an anatomical structure. Alternative means of deployment of the electrode means 200 and expansion thereof are contemplated by the present invention including, but not limited to, extending the rod 300 from the shaft 100, and rotating the rod 300 so that a helical electrode means 208, such as shown in FIG. 3D, may expand outwards.

In yet another embodiment of the catheter electrode device contemplated by the present invention, shown in FIG. 3E, the expanding means is a shape memory implanted in the conductive material of the expandable electrode 201. The expanded shape of the electrode is pre-selected and implanted in the conductive material of the electrode means 201 by methods known to those of skill in the art. The shape of the preferred embodiment of the expanded electrode includes, but is not limited to, the angular shape of FIG. 3E, arcuate ribs, a helix or any other shape that will provide electrical contact between the catheter electrode 201 and the interior wall of a blood vessel or any other anatomical structure. The electrode means will expand spontaneously when the shaft 100 of the catheter device is retracted relative to the electrode. A shape memory electrode may also include a rod 300 to aid in the retraction of said shaft 100 by preserving the length of the electrode means 201 as shaft retraction occurs.

(ii) Catheter Balloon Electrode. An electrode expansion means of the present invention is contemplated to be an inflatable balloon having electrically conductive wires or continuous or discontinuous strips thereon. Once a catheter electrode device is implanted in a blood vessel (or trachea or esophagus) the balloon is inflated with gas or liquid so as to make electrical contact between the electrode and the interior wall of the blood vessel.

The metal foil strips or wires on the balloon can be oriented relative to the long axis of the catheter device in any fashion that include longitudinal, circumferential, helical or arcuate ribs, or any other shape that will provide electrical contact between the catheter electrode 201 and the interior wall of a blood vessel or any other anatomical structure, and would be electrically isolated from each other. As with the basket wire electrodes described in (i) above, the electrodes are individually accessible from the hub of the catheter. Wire electrodes may be used as described for the basket array, with the expandable balloon pressing the electrically naked region of the wires against the interior wall of a blood vessel. Areas of the wires which do not make contact with the tissue walls may be, but not necessarily, insulated.

The expandable balloon is comprised of any expandable material known to one of skill in the art such as, but not limited to, latex, plastic, polymer or monomer that is acceptable for implanting into a human or animal. The balloon 400 may be comprised of a flexible metallic foil electrically connected to a means of applying an electric pulse 207, so that the surface of the balloon can function as an expandable electrode. In one embodiment, the balloon 400 comprises a flexible metallic foil with an insulating strip imposed thereon or a plurality of insulating layers, thereby forming a balloon having multiple electrodes electrically connected to a means of applying an electric pulse 207. Alternatively, the balloon 400 may be comprised of alternate strips of metallic foil and insulating material, each foil strip individually electrically connected to a means of applying an electric pulse 207

The balloon is selected from a variety of shapes including, but not limited to, an ovoid or spherical balloon located at the distal end of a catheter or tube. The balloon may encircle, in whole or in part, a catheter or a tube, thereby forming a collar. A collar balloon may be selected from a variety of shapes including, but not limited to, an oval, a cylinder, or any other form known to one of ordinary skill in the art.

The balloon may be of any length and diameter when expanded that will establish contact between the balloon and the interior wall of an anatomical structure. Preferably, the dimensions of the expanded balloon 400 will be such that the balloon 400 cannot cause physical trauma to said structure. The preferred length of the balloon is between about 1 cm and 10 cm, most preferably between about 2 cm and 8 cm. The preferred diameter of the expanded balloon is between about 1 cm and 8 cm, most preferably between about 2 cm and 6 cm.

For transvenous stimulation of the vagus nerve with an electrode mounted on a balloon, a delivery catheter may be used that is multiply fenestrated proximally and distally to the balloon, thereby avoiding total obstruction of blood flow. The balloon expansion means of the present invention offers the additional advantage that the balloon may have a pre-selected shape incorporating at least one, or a plurality of, grooves, notches, traversing tubes or tunnels, or any other form. Such indentations or traversing means of communication allow unobstructed blood flow while still maintaining contact between the expandable electrode and the interior wall of the blood vessel. Preferably the ridges number between 1 and 20, more preferably 1 and 12, and most preferably between 2 and 6 in number. When the balloon incorporates ridges, and the accompanying indentations, the electrode or plurality of electrodes are disposed on said ridges. While the present invention contemplates from 1 to about 10 electrodes on a ridge, the preferred number is from 1 to 5. The means to inflate a balloon may be within a catheter or tube or disposed on the exterior surface of said catheter or tube, and connected to a means to introduce a gas or liquid to inflate the balloon once the surgeon has placed the balloon electrode adjacent to a target nerve.

In one embodiment of the present invention, shown in FIG. 4A, the catheter electrode device, the device comprises at least one expandable electrode 201 longitudinally dispersed on an expandable balloon 400 at the distal end of the catheter shaft 100. In another embodiment, shown in FIG. 4B, the electrodes 206 are circumferential and are electrically connected to electric pulse applying means 207. In yet another embodiment, shown in FIG. 4C, the electrode 208 is helically arranged coaxially to the inflatable balloon 400 and the electrode is electrically connected to a means of supplying an electric pulse 207.

In a preferred embodiment of the present invention as shown in FIG. 4D and in cross-section FIG. 4E, the balloon 400 includes at least one raised rib 401, with an expandable electrode 201 exposed thereon, and wherein the expanded balloon is non-obstructive to the blood flow. The present invention contemplates that the inflatable balloon may have a plurality of raised ribs with electrode means thereon, and that the raised ribs may be, but not limited to, longitudinal, circumferential, or helical arrangements.

In yet another embodiment of the catheter balloon electrode device, the expandable electrode means 201 is a flexible wire mesh, or a metal foil that partially, substantially or completely covers the surface of the balloon 400. The present invention further contemplates that the expanding electrode means 201 may be any other flexible conductive material that will allow an electric pulse or field to be applied to a nerve.

In a preferred embodiment of the catheter balloon device, the expandable electrode means 201 may be from 1 to about 50 in number, most preferably 1 to 24 in number. The electrodes 201, when a plurality, are electrically isolated from each other. In the preferred embodiments, the expandable electrodes 201 are individually connected to a means of applying an electrical pulse that is connected to a multi-channel plug connector.

In embodiments of the catheter device, having an inflatable balloon, shown in FIG. 4F, the electrode 201 or plurality of electrodes are attached to the balloon so that when the balloon is inflated, the electrodes have a pre-selected arrangement. In a further embodiment, the electrodes 201 are not fixed to the inflatable balloon 400 but held in a pre-selected arrangement by means of at least one connecting, non-electrically conductive yoke 402 attached to the electrodes 201.

Figure 5B:
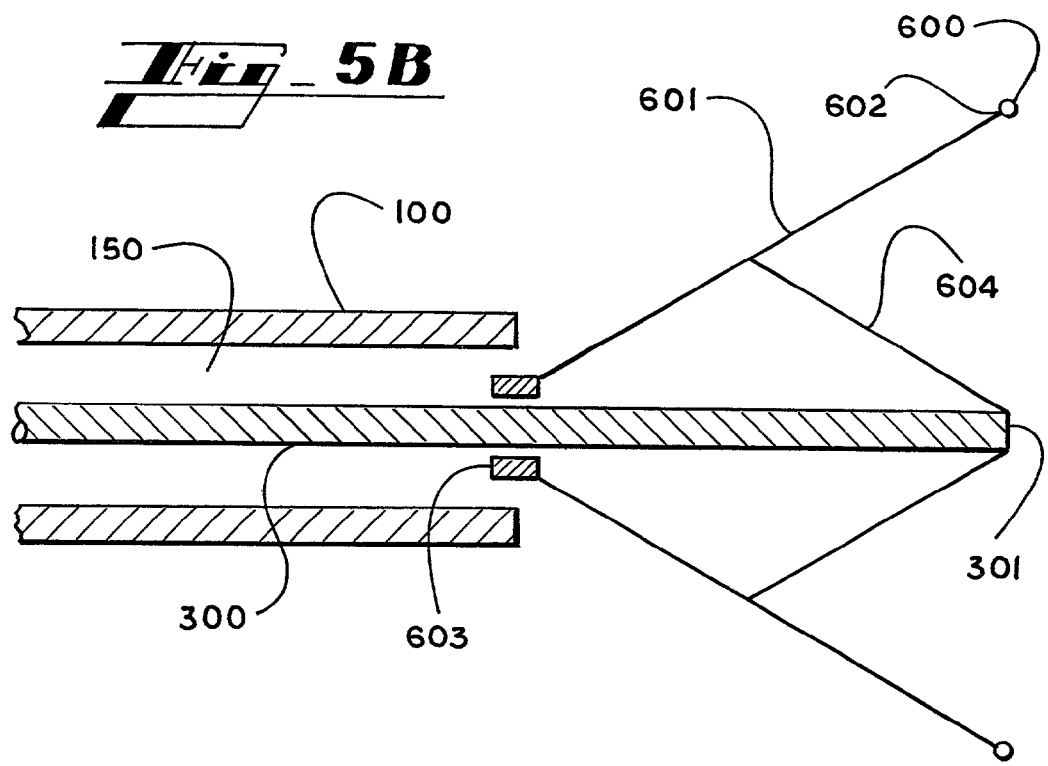

(iii) Catheter Umbrella Electrode. The present invention provides a catheter umbrella electrode means, as shown in FIGS. 5A and 5B. The umbrella electrode means comprises at least one, and preferably a plurality of, expandable electrode means, wherein each electrode 600 is mounted on a spoke 601 and electrically connected to a means of delivering an electric pulse 605 to the electrode 600, and wherein said means 605 comprises wires. The electrodes 600 may be, but not necessarily, disposed at the distal ends 602 of said spokes 601, The spokes 601 are composed of any electrically conductive or non-conductive material known to one of skill in the art. The spokes 601 include, but are not limited to, wires, strips or any other suitable form known to one skilled in the art. When electrically conductive, the spoke 601 comprises the means of delivering an electric pulse 605 and is coated with a non-conductive material. Individual spokes of a plurality of spokes are electrically isolated from all others. The expandable electrodes 600 are deployed in the fashion of an umbrella to contact the electrically exposed electrodes 600 of the umbrella spokes against the wall of a blood vessel or other anatomical feature. The umbrella spokes serve the same function as the ribs of the basket-type device shown in FIGS. 3A, 3B and 3E. Preferably, the spokes 601 number between 1 and about 50, more preferably between 4 and about 24.

One embodiment of the catheter umbrella electrode device, shown in FIG. 5A, has a shaft 100 with a lumen 150 and a rod 300 disposed therein and an umbrella electrode means. Said rod 300 has a distal end 301 with one, or a plurality of radially disposable spokes 601 attached thereto. The spokes 601 are able to move radially away from the rigid rod and thereby contact the interior wall of a blood vessel or other anatomical feature.

A slideable collar 603, coaxially disposed on the rod 300 is connected to the plurality of radially disposed spokes 601 by a plurality of connecting means. The connecting means comprises a linking wire 604 pivotally joined to the slideable collar 603 and to a spoke 601, one linking wire 604 attached to each spoke 601.

In another embodiment of the catheter umbrella electrode device, shown in FIG. 5B, the slideable collar 603 is pivotally attached to the plurality of spokes 601. Linking wires 604 are pivotally joined to the distal end 301 of the rod 300 and to the spokes 601. The shaft 100 may be positioned so that it overlays the wires or strips to form a protective sheath. In one embodiment, linking wires 604 can comprise the means of delivering an electric pulse 605.

By retracting the slideable collar 603 relative to the rod 300. The radially disposed spokes 601 are positioned parallel to the longitudinal axis of the rod 300. Wires 605 attached to the electrodes 600 may also be attached to the slideable collar 603 and used to retract or extend the collar 603 relative to the rod 300.

By retracting the rod 300 into the lumen 150 of the shaft 100, the shaft becomes a protective sheath around the spokes 601 so that the catheter may be implanted in a blood vessel or other anatomical structure without the electrodes 600 penetrating or otherwise injuring the wall of said structure.

When the surgeon has implanted the catheter adjacent to the vagus nerve, the rod 300 is extended to remove the spokes 601 and the electrodes 600 from the lumen 150 of the shaft 100 comprising the protective sheath, and the slideable collar 603 is positioned relative to the rod 300 so that the spokes 601 extend away from the rod 300, and the electrodes make electrical contact with the wall of the blood vessel or other anatomical structure.

Neural Clip Electrode.

After direct surgical exposure of the vagus nerve, an electrode means electrically connected to a pulse supply means can be placed in direct contact with the exterior surface of the nerve. Stimulation of the vagus nerve can be achieved by direct access to the vagus nerve through either a neck incision or via thoracoscopy, thoracotomy or through a sternotomy. The vagus nerve can be approached lateral to the pericardium and below the level of the right innominate artery to avoid the right recurrent laryngeal nerve. This can be accomplished thoracoscopically without the necessity of a formal sternotomy or neck incision.

The present invention provides clip electrode means, shown in FIGS. 6A–6C, for directly contacting an electrode means with a nerve, comprising a first electrically non-conductive member 700 pivotally secured by a pivot means 701 to a second electrically non-conductive member 702 to form confronting yaws. In one embodiment, an electrode 703, electrically connected to a means for applying an electric pulse 704 to said electrode 703, is attached to the first electrically non-conductive member 700 and in the confronting jaw region thereof. In another embodiment of the present invention, opposing electrodes are disposed on the electrically non-conductive members, 700 and 702 within the confronting jaw region.

The present invention reduces crush trauma to a nerve by the electrodes being compressible electrically conductive material that cushions the nerve tissue, as shown in FIG. 6A. In yet another embodiment of the clip electrode, at least one electrically non conductive member has a groove 705, shown in FIGS. 6B and 6C, wherein the groove 705 is lined with an electrode.

In all embodiments of the present invention, the electrode may be, but is not limited to, a concave form as shown in FIGS. 6B and 6C, a compressible electrically conductive material that cushions the nerve tissue, a wire, a strip, a wire mesh or wire wool, or any other conductive material or form that will not induce physical trauma to the neural tissue. In another embodiment, opposing grooves are in each nonconductive member 700 and 702. In all embodiments, the preferred means for applying an electric pulse 704 to an electrode 703 is a wire electrically connected to a multi-channel connector 706.

In yet another embodiment the clip electrode has at least two electrodes 703, electrically isolated from each other, as shown in FIG. 6D. Each electrode 703 can be independently electrically connected to a separate means of supplying an electric pulse. Thus, the electric pulse may be delivered to the nerve between at least two electrodes 703 on opposing electrically nonconductive members 700 and 702, as shown in FIG. 6C, or on one electrically nonconductive member as shown in FIG. 6D.

Neural Cuff Electrode.

The present invention further provides a cuff device, shown in FIGS. 7A and 7B, for the direct application of an electrode to a nerve. In one embodiment, the cuff device is a flexible or malleable wire mesh 800 capable of conforming to the surface of the nerve 801, as shown in FIG. 7A. In another embodiment, the cuff device is an electrically conductive sheet that can partially or completely envelop a nerve. In both embodiments, the electrode has a means 802 to electrically connect the electrode to a pulse generator. In either embodiment, the surface of the electrode in contact with the nerve is electrically exposed, while the opposite surface of the electrode is, but not necessarily, electrically insulated to avoid electrical stimulation of adjacent anatomical structures.

In another embodiment of the cuff device, as shown in FIGS. 7B and 7C, the cuff device has an electrically non-conductive member 803 having a traversing channel 804 and at least one electrode 805 and a means of applying an electric pulse 802 to said electrode 805 therein. In the most preferred embodiment, the electrode 805 is a wire mesh. In another preferred embodiment, the electrode 805 is a conductive sheet. In yet another preferred embodiment, such as shown in FIG. 7D, the cuff device has a first electrode 806 and a second electrode 807, wherein the electrodes are electrically isolated from each other, and each electrode is electrically connected to a separate means of applying an electric pulse 802.

Transdermal Array Electrode.

The present invention provides electrode arrays supported by a non-conductive support means such as, but not limited to, a pad. The pad can be adhesive and can be applied to the surface of the skin so that the array of electrodes is in electrical contact thereon. To increase electrical conductivity between the electrodes and the skin, an intervening conductive gel, known to one of skill in the art, can be included. The cutaneous electrode array can be placed on or around the neck in the vicinity of the vagus nerve. When placed around the neck, the non-conductive support may include a Velcro strap or any other fastening device to secure the pad to the patient. The pad can be shaped to accommodate the neck region of the patient.

The transcutaneous electrode array may be used to provide a unipolar electrode, wherein a second catheter electrode is implanted in the patient adjacent to the nerve to be stimulated. An electric pulse is applied to an individual electrode of the array of electrodes and the implanted catheter electrode is grounded. Alternatively, the electric pulse is applied to the implanted catheter electrode, and one or more of the array electrodes is grounded.

The transcutaneous electrode array provided by the present invention may also be used to apply a bipolar electric pulse to a nerve, wherein the anode and cathode electrodes are selected from the electrodes of the array. Connection to the vagus nerve stimulation device allows the interrogatory unit therein to selectively determine the optimum pair of electrodes to achieve maximum stimulation of the target nerve, most preferably the vagus nerve. The present invention also provides an electrode array device, such as shown in FIGS. 8A–C for delivering an electric pulse through the skin to a nerve. The electrode array device comprises an electrically non-conductive support 900 having a plurality of electrodes 901, wherein said electrodes 901 are electrically isolated from each other. Each electrode 901 is connected to a means of supplying an electric pulse 902, wherein said means 902 is a wire and the plurality of wires are electrically connected at their proximal ends to a multi-channel connector 903. The electrically non-conductive support 900 may be, but is not limited to, a sheet, a pad, a block such as a cube or a cylinder, and may be any geometric form such as, but not only, a square, oblong, broad strip, circular or ovoid disc.

In one preferred embodiment, as shown in FIG. 8A, the electrically non-conductive support 900 is a sheet and the array of electrodes 901 are exposed on one face of said sheet. Each electrode 901 is connected to a means of supplying an electric pulse 902, wherein said means 902 is a wire and the plurality of wires are electrically connected at their proximal ends to a multi-channel connector 903. In another preferred embodiment of the electrode array device of the present invention, the means of applying an electric pulse 802, shown in FIG. 8B, is a sheet with a traversing hole 904. In yet another embodiment, as in FIG. 8C, a means of communication 905 connects the traversing hole 904 to the outer edge 906 of the electrically non-conductive support 900. This connecting means may be, but is not limited to a slit, a slot, or a channel. The communication means 905 and traversing hole 904 are intended to allow easy placement of an electrode on a patient's neck.

In another preferred embodiment, as shown in FIG. 8D, the electrically non-conductive support 900 is in a necklace-like configuration and the array of electrodes are exposed on one face thereof. A In another preferred embodiment, as shown in FIG. 8E, the electrically non-conductive support 900 is in a turtleneck-like configuration and the array of electrodes are exposed on one face thereof. Each electrode 901 is connected to a means of supplying an electric pulse 902, wherein said means 902 is a wire and the plurality of wires are electrically connected at their proximal ends to a multi-channel connector 903.

In each of the embodiments shown in FIGS. 8A-8E, the electrodes may be in a variety of shapes, such as circular, square or elongated. Furthermore, the electrode array can have fasteners 907 such as, but not limited to, Velcro, straps or buckles, that will allow the non-conductive support to be secured to a human or animal. Alternatively, the invention provides that an inflatable collar can be positioned on each of the embodiments shown in FIGS. 8A–8E, that will allow the non-conductive support to be secured to a human or animal.

In all embodiments of the Transdermal Array Electrode, it is anticipated that the width of the non-conductive support 900 will be between about 1.5 cm and about 10 cm, preferably between about 2 cm and about 5 cm. It is anticipated that the length of the non-conductive support 900 will be between about 1 cm and about 10 cm, preferably between about 2 cm and about 5 cm. In the case of the necklace configuration, this length of the non-conductive support is between about 15 cm and about 45 cm. It is further anticipated that the depth of the non-conductive support 900 will be between about 0.1 cm and about 3 cm, preferably between about 0.2 cm and about 1.5 cm.

Another embodiment of the cutaneous array electrode is a single electrode applied to the surface of the skin. In yet another embodiment, a plurality of electrodes in an array can be electrically connected to act as a single electrode. The electrode array device of the present invention may have an optional electrically conductive gel layer and an optional electrically conductive adhesive layer to increase the efficiency of electrical contact with the skin.

Endotracheal and Nasogastric Tube Electrodes.

The present invention contemplates embodiments of the balloon, basket, umbrella and steerable devices as described above, combined with endotracheal tubes used for maintaining ventilation during general anesthesia, or with a nasogastric or esophageal tube used for gastric decompression. While the sizes of the expandable basket or umbrella electrode devices used in conjunction with endotracheal or nasogastric tubes are adapted for use in the trachea or esophagus, the concepts and designs are similar.

One approach to the stimulation of the vagus nerve is to access the internal jugular vein with a catheter electrode. The internal jugular vein runs parallel to, and is intimately associated with, the vagus nerve along the length of the vein in the neck of humans. The trachea and esophagus, however, also lie in close proximity to the vagus nerve in humans. These anatomical structures are ideally suited for the location of catheter or tube electrodes useful for stimulating the vagus nerve. By accessing the trachea or the esophagus, there is no requirement for a neck incision to insert an intravascular catheter or direct surgical isolation of the vagus nerve. Tracheal or esophageal electrodes may be combined with a cutaneous electrode device to provide unipolar neural electrostimulation. Several different devices of the present invention utilize these alternative and less invasive routes.

The present invention further provides an endotracheal or nasogastric tube electrode device, as shown in FIG. 9A, comprising an endotracheal or nasogastric tube 1000 having an inflatable collar 1001 which may be, but is not limited to, a balloon design, and a means to inflate 1002 said collar 1001, at least one expandable electrode means 1003 on said collar 1001. The electrode means 1003 is so positioned that when the collar 1001 is inflated the electrode means 1003 is in contact with the interior lining of the trachea. The electrode means 1003 is electrically connected to a means of supplying an electric pulse 1004 and a multi-channel connector means 1005.

The electrode expansion means 1001 should not be construed as being only an inflatable collar. The present invention contemplates using a balloon, umbrella, barrel or basket electrode. The present invention provides a catheter umbrella electrode means, as shown in FIG. 9B. The umbrella electrode means comprises at least one, and preferably a plurality of, expandable electrodes 1007, each electrode 1007 mounted on a spoke 1008 and electrically connected to a means of supplying an electric pulse 1009 to the electrodes 1007, wherein the electrodes 1007 are disposed at the distal ends 1010 of said spokes 1008, and wherein said means 1009 comprises wires. The spokes 1008 are composed of an electrically conductive or non-conductive material. The spokes 1008 are, but not limited to, wires, strips or any other suitable form known to one skilled in the art. When electrically conductive, the spokes 1008 are coated with a non-conductive material. Each spoke is electrically isolated from all others. The expandable electrodes 1007 are deployed in the fashion of an umbrella to contact the electrically naked tips of the umbrella spokes against the wall of a blood vessel or other anatomical feature.

One embodiment of the endotracheal or nasogastric tube umbrella electrode device, shown in FIG. 9B, has an endotracheal or nasogastric tube 1000, and a plurality of radially disposable spokes 1008 attached thereto. The spokes 1008 are able to move radially away from the rigid rod and thereby contact the interior wall of the trachea.

A slideable collar 1011, coaxially disposed on the endotracheal or nasogastric tube 1000 is connected to the plurality of radially disposed spokes 1008 by a plurality of connecting means. The connecting means comprises a linking wire 1012 pivotally joined to the slideable collar 1011 and to a spoke 1008, one linking wire 1012 attached to each spoke 1008.

By retracting the slideable collar 1011 relative to the region of the endotracheal or nasogastric tube 1000 in the patient, the radially disposed spokes 1008 are positioned parallel to the longitudinal axis of the tube 1000. Wires 1009 attached to the electrodes 1007 may also be attached to the slideable collar 1011 and used to retract or extend the collar 1011 relative to the tube 1000.

When the surgeon has inserted the endotracheal or nasogastric tube 1000 in the trachea adjacent to the vagus nerve, the slideable collar 1011 is positioned relative to the tube 1000 so that the spokes 1008 extend away from the tube 1000, and the electrodes 1007 make electrical contact with the wall of the blood vessel or other anatomical structure.

The electrodes may be arranged longitudinally relative to the central longitudinal axis of the endotracheal or nasogastric tube. The electrodes may be circumferentially arranged in a coaxial relationship with the tube 1000. The electrodes may be spirally arranged around the inflatable balloon or collar. The inflatable collar may be inflated by the inflation means 1002 with air, gas or a liquid.

The present invention also provides an endotracheal or nasogastric tube 1000, as shown in FIG. 9C. This embodiment provides for expandable or rigid electrodes which are substantially embedded within the tube material to avoid living tissue irritation. The electrode means comprises at least one, and preferably a plurality of, electrodes 1003, each electrode 1003 electrically connected to a means of supplying an electric pulse 1009 to the electrodes 1003, wherein the electrodes 1003 are exposed to the exterior surface of the tube 1000 adjacent the distal end of said tube 1000, and wherein said means 1009 comprises wires. The electrode means are electrically independent of each other.

A preferred embodiment of the expandable electrode means and the electrode expanding means wherein the electrode means is a basket catheter electrode with at least one expandable rib. In a preferred embodiment, the expandable rib or plurality of such ribs are electrically conductive wires. Thin wires are preferred with a thickness of between about $1/128$ inch and $1/8$ inch, most preferably between about $1/64$ and $1/16$ inch. In another preferred embodiment, the expandable ribs are electrically conductive strips from about $1/128$ inch to about $1/4$ inch wide, most preferably from about $1/64$ inch to about $1/4$ inch. In yet another preferred embodiment the expandable ribs are electrically non-conductive strips with electrodes dispersed thereon. In a most preferred embodiment, the electrically conductive wire or strip is comprised of a proximal region, a central region and a distal region, wherein the proximal region and the central region form a first angle and the central region and the distal region form a second angle. Preferably the first and second angles are between about 1° and about 180°. Most preferably, the first and second angles are between about 90° and about 120°.

Preferably, the ribs are between 1 and about 48 in number, more preferably between 2 and about 12 in number. In a preferred embodiment, the length of the expanded electrode is between about 1 and about 15 cm. More preferably, the length is between about 2 and about 6 cm. The diameter of the catheter before expansion is the diameter of the catheter shaft and is 0.5 mm to about 3 mm, most preferably 1 mm.

In one embodiment of the present invention, the central region is electrically exposed, and the proximal region and distal region are electrically insulated. In this embodiment, the length of electrically exposed central region is between 0.1 cm and about 10 cm, most preferably between 0.5 and about 5 cm. The means of applying an electrical pulse are preferably, but not limited to, wires electrically connected to the expandable ribs. The wires are electrically independent of one another, and pass through the shaft. The wires and are electrically connected to a multi-channel electrical connection.

Method of Inducing Asystole by Vagal Electro-Stimulation and CIA Pharmaceutical Composition Treatment The present invention provides a method for the induction of cardiac asystole by the application of an electric pulse or field to the vagus nerve. The CIA pharmaceutical composition provides a background pharmaceutical state wherein the impact of vagal nerve stimulation is potentiated and heart will not spontaneously escape from the electrically induced asystole. Throughout subsequent cardiac surgery, the surgeon monitors the heart function and can selectively reinitiate the heart beat by means of a cardiac pacer device, slaved to the vagal nerve stimulator. This can also be performed automatically if the heart beat fails to resume within a preset time period.

The present invention, therefore, provides a method of inducing and prolonging asystole by implanting a catheter or tube expanding electrode into a blood vessel, trachea, or esophagus of a human or animal or by applying a cutaneous electrode. The electrodes are positioned adjacent to the vagus nerve by the surgeon, and said electrodes are connected to the vagus nerve stimulator by means of multi-channel connectors and an output. At least one output from the stimulator is used, preferably two outputs, each connected to a separate electrode device.

The surgeon adjusts the vagal nerve stimulator to deliver a first unipolar or multipolar electric pulse to an implanted cutaneous electrode and the output of the heart is monitored by the microprocessor. Random selection of electrodes is then followed by additional pulses until a maximum state of asystole is achieved. The CIA pharmaceutic composition that comprises an acetylcholinesterase inhibitor, a β-adrenogenic receptor blocker and a calcium channel blocker, is administered before or after the initial testing. An electric pulse of optimum amplitude and frequency is applied to the previously selected electrode combination and controlled intermittent asystole, with minimal or no escape, results. Once the surgical procedure is completed, or predetermined point selected by the surgeon or preselected automatically by the vagus nerve stimulator, the heart is removed from asystole by a cardiac pacer means operated by the surgeon or by the vagus nerve stimulator.

The above description provides certain preferred embodiments of the devices and methods of the present invention. However, it is understood that many modifications and additional embodiments can be routinely made in view of the disclosure, and all such embodiments are intended to be encompassed within the spirit of the invention.

I claim:

1. A device for electrically stimulating the vagus nerve of a patient, comprising:

an elongated body member of sufficient length to extend from a point outside of a patient to a location within one of the trachea, esophagus, and internal jugular vein of said patient, said elongated body member having a proximal end and a distal end, said body member having an outer diameter adjacent said distal end of said body member smaller than the inner diameter of said one of said trachea, said esophagus, and said internal jugular vein;

an expandable support member adjacent said distal end of said body member, said expandable support member normally being contracted to an outer diameter smaller than the inner diameter of said one of said trachea, said esophagus, and said internal jugular vein, and said expandable support member being selectively expandable when said distal end of said body member is inserted into said one of said trachea, said esophagus, and said internal jugular vein to contact the wall of said one of said trachea, said esophagus, and said internal jugular vein around substantially the entire circumference of said expandable support member; and an electrode mounted on said expandable support member, at least a portion of said electrode being disposed on said portion of said expandable support member that contacts said wall of said one of said trachea, said esophagus, and said internal jugular vein when said expandable support member is inserted into said one of said trachea, said esophagus, and said internal jugular vein and expanded; and means for placing said electrode in conductive communication with a source of electrical energy so as to energize said electrode;

whereby when said distal end of said body member is inserted into said one of said trachea, said esophagus, and said internal jugular vein, and said expandable support member is expanded, said electrode is firmly imposed against said wall of said one of said trachea, said esophagus, and said internal jugular vein.

2. The device of claim 1, wherein said elongated body member is dimensioned for use in the esophagus, and wherein said device further comprises a hollow internal lumen extending from a proximal opening at a proximal portion of said elongated body member to a distal opening at a distal portion of said elongated body member;

whereby liquid and gas can be suctioned from the stomach and esophagus through said lumen so as to decompress the gastrointestinal tract, and whereby medications can be enterally administered through said lumen.

3. The device of claim 1, wherein said elongated body member is dimensioned for use in the trachea, and wherein said device further comprises a hollow internal lumen extending from a proximal opening at a proximal portion of said elongated body member to a distal opening at a distal portion of said elongated body member;

whereby said device serves to maintain an airway during anesthesia, allowing positive-pressure ventilation of the patient's lungs.

4. The device of claim 3, further comprising an inflatable balloon cuff located on a distal portion of said elongated body member, said balloon cuff being inflatable and deflatable via a second lumen extending from a proximal portion of said elongated body member to a location inside said balloon cuff.

5. The device of claim 1,
wherein said elongated body member is dimensioned for use in an internal jugular vein, and wherein said device further comprises a hollow central lumen extending from a proximal opening at a proximal portion of said elongated body member to a distal opening at a distal portion of said elongated body member, through which intravenous liquids and medications can be administered to a patient.

6. The device of claim 1,
wherein said elongated body member is dimensioned for use in said internal jugular vein, and wherein said device further comprises:
a hollow channel in said elongated body member, said channel being in fluid communication with the ambient through a hole in the side of and proximal to the distal end of said elongated body member,
whereby central venous pressure can be monitored through said hollow channel.

7. The device of claim 1,
wherein said elongated body member is dimensioned for use in the internal jugular vein, and wherein said device further comprises:
an inflatable balloon located on a distal portion of said elongated body member; and
means at said distal end of said elongated body member for monitoring pulmonary artery pressures.

8. The device of claim 1,
wherein said expandable support member comprises an inflatable cuff, and
wherein said expandable support member is selectively expandable by inflating said cuff.

9. The device of claim 8,
wherein said inflatable cuff comprises at least one raised ridge which engages said wall of said one of said trachea, esophagus, and internal jugular vein when inserted therein and expanded, said raised ridge permitting fluid to flow past said inflatable cuff; and
wherein at least a portion of said electrode is mounted on said raised ridge,
whereby said raised ridge presses said electrode against said wall of said one of said trachea, esophagus, and internal jugular vein to facilitate an optimal electrical contact.

10. The device of claim 9,
wherein said elongated body member is dimensioned to be received within said internal jugular vein, and
wherein said raised ridges define at least one flow path between a distal end of said inflatable cuff and a proximal end thereof,
whereby blood in an internal jugular vein flows past said inflatable cuff, such that inflation of said inflatable cuff within said internal jugular vein does not block venous drainage from the head.

11. The device of claim 9, wherein said raised ridge is longitudinally oriented with respect to said inflatable cuff.

12. The device of claim 9, wherein said raised ridge is circumferentially oriented with respect to said inflatable cuff.

13. The device of claim 9, wherein said raised ridge is helically oriented with respect to said inflatable cuff.

14. The device of claim 8, wherein said electrode comprises an expandable wire mesh that covers at least a portion of said inflatable cuff and which expands as said cuff is inflated.

15. The device of claim 8, wherein said electrode comprises a metal foil disposed on said inflatable cuff.

16. The device of claim 8, wherein said electrodes are maintained on said inflatable cuff by a non-conductive yoke.

17. The device of claim 1, further comprising a plurality of electrodes spaced around the circumference of said expandable support member.

18. The device of claim 17, wherein said plurality of electrodes comprises from 2 to 50 electrodes.

19. The device of claim 17, wherein said plurality of electrodes comprises from 2 to 24 electrodes.

20. The device of claim 17, wherein each of said plurality of electrodes is electrically isolated from and capable of being electrically energized independently of the others of said plurality of electrodes.

21. The device of claim 17,
wherein each of said plurality of electrodes is electrically insulated along its entire length and circumference except for at least one uninsulated portion over the exterior aspect of the middle portion of each electrode adjacent the middle portion of said inflatable cuff,
whereby said at least one uninsulated portion contacts the interior of the wall of said trachea, esophagus or internal jugular vein when said stimulation device is appropriately positioned inside a patient and said wire frame is expanded.

22. The device of claim 17, wherein said plurality of electrodes are substantially longitudinally oriented with respect to said support member.

23. The device of claim 17, wherein said plurality of electrodes are substantially circumferentially oriented with respect to said support member.

24. The device of claim 1, wherein said electrode is substantially longitudinally oriented with respect to said support member.

25. The device of claim 1, wherein said electrode is substantially circumferentially oriented with respect to said support member.

26. The device of claim 1, wherein said electrode is substantially helically oriented with respect to said support member.

27. The device of claim 1, wherein said plurality of electrodes are substantially helically oriented with respect to said support member.

28. The device of claim 1, wherein said expandable support member comprises a plurality of ribs connected to said elongated body member so as to form an expandable frame.

29. The device of claim 28, wherein said expandable frame comprises at least one rib which is substantially longitudinally oriented with respect to said elongated body member.

30. The device of claim 28, wherein said expandable frame comprises at least one rib which is substantially circumferentially oriented with respect to said elongated body member.

31. The device of claim 28, wherein said expandable frame comprises at least one rib which is substantially helically oriented with respect to said elongated body member.

32. The device of claim 28, wherein said electrode is mounted to and follows at least a portion of a rib of said expandable frame.

33. The device of claim 32, wherein said rib which said electrode follows is comprised of an electrically insulated material.

34. The device of claim 28, wherein said ribs forming said expandable frame are comprised of an electrically insulating material.

35. The device of claim 34, wherein said electrode comprises a metal foil disposed on said expandable frame.

36. The device of claim 34, further comprising a plurality of electrodes spaced around the circumference of said expandable support member.

37. The device of claim 36, wherein said plurality of electrodes comprises from 2 to 50 electrodes.

38. The device of claim 36, wherein said plurality of electrodes comprises from 2 to 24 electrodes.

39. The device of claim 36, wherein each of said plurality of electrodes is electrically isolated from and capable of being electrically energized independently of the others of said plurality of electrodes.

40. The device of claim 34, wherein said electrode comprises a wire mesh disposed on said expandable frame.

41. The device of claim 28,
wherein said expandable frame comprises a forward portion, a rearward portion, and an intermediate portion;
wherein said device further comprises a first elongated member mechanically linked to said forward portion of said frame;
wherein said device further comprises a second elongated member mechanically linked to said rearward portion of said frame; and
wherein said first and second elongated members are longitudinally movable with respect to one another so as to draw said forward and rearward portions of said frame toward one another so as to cause said intermediate portion of said frame to bow outward.

42. The device of claim 28,
wherein a plurality of said ribs are mechanically linked at their forward ends;
wherein said device further comprises an elongated member longitudinally displaceable with respect to said forward ends of said ribs; and
wherein said device further comprises a plurality of struts, one end of each of said struts being mechanically attached to said elongated member and the opposite end of each of said struts being attached to a corresponding one of said ribs,
said struts, said ribs, and said longitudinal member being configured such that extending said longitudinal member causes said struts to displace said ribs radially outward.

43. The device of claim 1,
wherein said elongated body member further comprises a lumen extending from said proximal end to said distal end;
wherein said device further comprises an elongated shaft slidably disposed within said lumen, said elongated shaft having a proximal end and a distal end, and said shaft having a length greater than the length of said elongated body member,
wherein said expandable support member comprises:
a plurality of ribs each having an inner end pivotably connected to one of said distal end of said elongated body member and said distal end of said shaft,
a plurality of struts each having an inner end pivotably connected to the other of said distal end of said elongated body member and said distal end of said shaft,
an outer portion of each of said plurality of struts being pivotably connected to an outer portion of a corresponding one of said plurality of ribs,
whereby retracting said shaft relative to said elongated body member so as to bring said distal end of said shaft closer to said distal end of said body member causes said struts to displace said outer ends of said ribs radially outward; and
wherein said electrode mounted on said expandable support member comprises said electrode being operatively associated with an outer portion of one of said ribs;
whereby retracting said longitudinal member brings said electrode into contact with the wall of said one of said trachea, esophagus, and internal jugular vein.

44. The device of claim 43, wherein said inner ends of said plurality of ribs are pivotably connected to said distal end of said elongated body member, and wherein said inner ends of said plurality of struts are pivotably connected to said distal end of said shaft.

45. The device of claim 43, wherein said inner ends of said plurality of ribs are pivotably connected to said distal end of said shaft, and wherein said inner ends of said plurality of struts are pivotably connected to said distal end of said elongated body member.

46. The device of claim 43, wherein said means for placing said electrode in conductive communication with a source of electrical energy comprises an electrical wire extending through said lumen in said elongated body member and being connected to said electrode on said outer portion of one of said plurality of ribs.

47. A device for electrically stimulating the vagus nerve of a patient, comprising:
an elongated body member having a proximal end and a distal end, said elongated body member being of sufficient length to extend from a point outside of a patient to a location within one of the trachea, esophagus, and internal jugular vein of said patient and having a diameter adjacent a forward end of said body member sufficiently small so as not to contact the entire wall of said one of said trachea, esophagus, and internal jugular vein when inserted therein;
a normally expanded, selectively contractible support member adjacent said distal end of said body member;
said support member in its normally expanded configuration having an outer circumference sufficient to contact substantially the entire inner circumference of said one of said trachea, said esophagus, and said internal jugular vein when said distal end of said body member is positioned within said one of said trachea, said esophagus, and said internal jugular vein;
said support member being selectively contractible when said distal end of said body member is inserted into said one of said trachea, said esophagus, and said internal jugular vein so as not to contact the entire wall of said one of said trachea, said esophagus, and said internal jugular vein;
means operatively associated with said support member and operable from outside said patient for selectively contracting said support member and for permitting said support member to return to its normal, expanded configuration;
an electrode mounted on said support member, at least a portion of said electrode being disposed on a portion of said support member that contacts said wall of said one of said trachea, said esophagus, and said internal jugular vein when said support member is inserted into said one of said trachea, said esophagus, and said internal jugular vein and permitted to expand to its normal configuration; and means for placing said electrode in conductive communication with a source of electrical energy so as to energize said electrode;

whereby when said support member is contracted and said distal end of said body member is inserted into said one of the trachea or esophagus or internal jugular vein and said electrode support section is then permitted to expand to its normal configuration, said electrode is firmly imposed against said wall of said one of the trachea or esophagus or internal jugular vein.

48. The device of claim 47, wherein said means operatively associated with said support member and operable from outside said patient for selectively contracting said support member and for permitting said support member to return to its normal, expanded configuration comprises a tube positionable around said support member to contract said support member and to retain said support member in a contracted condition, said tube being selectively displaceable with respect to said support member from a location outside said patient to uncover said support member so as to permit said support member to expand to its normal configuration.

49. The device of claim 47, wherein said support member comprises a plurality of resilient ribs connected to said elongated body member so as to form a normally expanded, selectively contractible support frame.

50. The device of claim 49, wherein said support frame comprises at least one rib which is substantially circumferentially oriented with respect to said elongated body member.

51. The device of claim 49, wherein said support frame comprises at least one rib which is substantially helically oriented with respect to said elongated body member.

52. The device of claim 49, wherein said electrode is mounted to and follows at least a portion of a rib of said support frame.

53. The device of claim 52, wherein said rib which said electrode follows is comprised of an electrically insulated material.

54. The device of claim 49, wherein said ribs forming said expandable frame are comprised of an electrically insulating material.

55. The device of claim 49, further comprising a plurality of electrodes spaced around the circumference of said support member.

56. The device of claim 55, wherein said plurality of electrodes comprises from two to fifty electrodes.

57. The device of claim 55, wherein said plurality of electrodes comprises from two to twenty-four electrodes.

58. The device of claim 55, wherein each of said plurality of electrodes is electrically isolated from and capable of being electrically energized independently of the others of said plurality of electrodes.

59. The device of claim 49, wherein said resilient ribs are comprised of a shape memory metal.

60. The device of claim 49, wherein shape memory metal is electrically insulated.

61. A device for electrically stimulating the vagus nerve of a patient, comprising:

an elongated body member of sufficient length to extend from a point outside of a patient to a location within one of the trachea, esophagus, and internal jugular vein of said patient and having an outer diameter adjacent a forward end of said body member smaller than the inner diameter of said one of said trachea, said esophagus, and said internal jugular vein;

an expandable frame adjacent a distal end of said body member, said expandable frame normally being contracted to an outer diameter smaller than the inner diameter of said one of said trachea, said esophagus, and said internal jugular vein, and said expandable frame being selectively expandable when said forward end of said body member is inserted into said one of said trachea, said esophagus, and said internal jugular vein to contact the wall of said one of said trachea, said esophagus, and said internal jugular vein around substantially the entire circumference of said expandable wire frame;

said expandable frame being formed from at least one wire which is electrically uninsulated at a location which contacts the wall of said one of said trachea, said esophagus, and said internal jugular vein when said forward end of said body member is inserted into said one of said trachea, said esophagus, and said internal jugular vein and expanded to contact the wall of said one of said trachea, said esophagus, and said internal jugular vein, and means for placing said electrode in conductive communication with a source of electrical energy so as to energize said electrode.

62. The device of claim 61, wherein said expandable frame comprises a plurality of wires.

63. The device of claim 62, wherein each of said plurality of wires of said wire frame is electrically insulated and isolated from the others of said plurality of wires, and wherein each of said plurality of wires can be individually electrically energized independently from the others of said plurality of wires.

64. The device of claim 62, wherein each wire of said wire frame is electrically insulated over its entire length and circumference except along the exterior aspect of a central portion of each wire where it contacts the interior of the wall of said one of said trachea, esophagus, and internal jugular vein when said stimulation device is appropriately positioned inside a patient and said wire frame is expanded.

65. The device of claim 61, wherein said at least one wire is substantially longitudinally oriented with respect to said elongated body member.

66. The device of claim 61, wherein said at least one wire is substantially circumferentially oriented with respect to said elongated body member.

67. The device of claim 61, wherein said at least one wire is substantially helically oriented with respect to said elongated body member.

68. The device of claim 61, wherein said expandable wire frame comprises a forward portion, a rearward portion, and an intermediate portion;

wherein said device further comprises a first elongated member linked to said forward portion of said wire frame;

wherein said device further comprises a second elongated member linked to said rearward portion of said wire frame; and wherein said first and second elongated members are longitudinally movable with respect to one another so as to draw said forward and rearward portions of said wire frame toward one another so as to cause said intermediate portion of said wire frame to bow outward.

69. The device of claim 61,
wherein said expandable wire frame comprises a plurality of wires linked at their forward ends;
wherein said device further comprises an elongated member longitudinally displaceable with respect to said forward ends of said wires; and
wherein said device further comprises a plurality of struts, one end of each of said struts being attached to said elongated member and the opposite end of each of said struts being attached to a corresponding one of said wires,
said struts, said wires, and said longitudinal member being configured such that extending said longitudinal member causes said struts to displace said wires radially outward.

70. The device of claim 61,
wherein said expandable wire frame comprises a plurality of wires linked at their rearward ends;
wherein said device further comprises an elongated member longitudinally displaceable with respect to said rearward ends of said wires; and
wherein said device further comprises a plurality of struts, one end of each of said struts being attached to said elongated member and the opposite end of each of said struts being attached to a corresponding one of said wires,
said struts, said wires, and said longitudinal member being configured such that retracting said longitudinal member causes said struts to displace said ribs radially outward.

71. A device for electrically stimulating the vagus nerve of a patient, comprising:
an elongated body member of sufficient length to extend from a point outside of a patient to a location within one of the trachea, esophagus, and internal jugular vein of said patient and having a diameter adjacent a forward end of said body member sufficiently small so as not to contact the entire wall of said one of the trachea, esophagus, and internal jugular vein when inserted therein;
a normally expanded, selectively contractible wire frame adjacent a forward end of said body member, said wire frame being formed from at least one wire, said wire frame in a contracted state having a diameter adjacent a forward end of said body member sufficiently small so as not to contact the entire wall of said one of the trachea, esophagus, and internal jugular vein when inserted therein, and said wire frame being configured such that when said forward end of said body member is inserted into said one of the trachea or esophagus or internal jugular vein and permitted to expand to a normal configuration, said wire frame contacts the wall of said one of the trachea or esophagus or internal jugular vein; and
means for placing said at least one wire of said wire frame in conductive communication with a source of electrical energy so as to electrically energize said one wire;
whereby when said forward end of said body member is inserted into said one of the trachea, esophagus, and internal jugular vein and said wire frame is permitted to expand to its normal configuration, said at least one wire is firmly imposed against said wall of said one of the trachea, esophagus, and internal jugular vein.

72. The device of claim 71, wherein said expandable frame comprises a plurality of wires.

73. The device of claim 72, wherein each of said plurality of wires of said wire frame is electrically insulated and isolated from the others of said plurality of wires, and wherein each of said plurality of wires can be individually electrically energized independently from the others of said plurality of wires.

74. The device of claim 72, wherein each wire of said wire frame is electrically insulated over its entire length and circumference except along the exterior aspect of a central portion of each wire where it contacts the interior of the wall of said one of said trachea, esophagus, and internal jugular vein when said stimulation device is appropriately positioned inside a patient and said wire frame is expanded.

75. The device of claim 71, further comprising a tube positionable around said wire frame to retain said wire frame in a compressed position and selectively displaceable with respect to said wire frame to expose said wire frame and thereby permit said wire frame to expand to its normal configuration.

76. The device of claim 71, wherein said at least one wire is substantially longitudinally oriented with respect to said elongated body member.

77. The device of claim 71, wherein said at least one wire is substantially circumferentially oriented with respect to said elongated body member.

78. The device of claim 71, wherein said wire frame is comprised of a shape memory metal.

79. The device of claim 71,
wherein said contractible wire frame comprises a proximal portion, a distal portion, and an intermediate portion;
wherein said device further comprises an elongated shaft linked to said distal portion of said wire frame;
wherein said proximal portion of said wire frame is fixed relative to said distal end of said elongated member; and
wherein said elongated shaft is longitudinally extensible with respect to said elongated body member so as to displace said proximal and distal portions of said wire frame away from one another so as to cause said intermediate portion of said wire frame to contract inward.

80. A device for electrically stimulating the vagus nerve of a patient, comprising:
an electrode positionable adjacent a vagus nerve of a patient;
an electrical pulse generator in conductive communication with said electrode, said pulse generator being capable of generating an electrical stimulus effective to cause controlled intermittent asystole when transmitted to said electrode and thereby communicated to said vagus nerve;
a cardiac monitoring device; and
a cardiac pacer for pacing the heart of said patient out of asystole;
whereby said patient's heart can be put into asystole by actuating said electrical pulse generator and paced out of asystole by said cardiac pacer.

81. The device of claim 80, further comprising a foot switch operatively associated with said electrical pulse generator for actuating said generator to transmit an electrical stimulus to said electrode.

82. The device of claim 80, wherein said pulse generator remains active so long as said foot switch is closed, whereby the duration of said electrical stimulus generated by said pulse generator can be controlled by controlling the duration of closing said foot switch.

83. The device of claim 80, further comprising a foot switch operatively associated with said cardiac pacer for actuating said cardiac pacer to pace said patient's heart out of asystole.

84. The device of claim 80, further comprising control circuitry operatively associated with said electrical pulse generator and said cardiac pacer, said control circuitry being operative to turn said cardiac pacer off when said electrical pulse generator is turned on.

85. The device of claim 80, further comprising control circuitry operatively associated with said electrical pulse generator, said cardiac monitoring device, and said cardiac pacer, said control circuitry being operative to automatically activate said cardiac pacer if said cardiac monitoring device does not sense a heartbeat within a predetermined time after cessation of vagal nerve stimulation.

86. The device of claim 80, further comprising a foot pedal operatively associated with said electrical pulse generator and said cardiac pacer, said switch being operative to activate said pulse generator and deactivate said cardiac pacer in response to a first press and release of said pedal, and to activate said cardiac pacer and deactivate said pulse generator in response to a second press and release of said pedal.

87. The device of claim 80, further comprising switch means responsive to voice activation operatively associated with said electrical pulse generator and said cardiac pacer, said switch being operative to activate said pulse generator and to deactivate said cardiac pacer in response to a first verbal command, and to activate said cardiac pacer and to deactivate said pulse generator in response to a second verbal command.

88. The device of claim 80, further comprising control circuitry operatively associated with said electrical pulse generator and said cardiac monitoring device, said control circuitry being operative to automatically control one or more of the frequency, amplitude, and amperage of said electrical pulse.

\* \* \* \* \*